(12) United States Patent
Goto et al.

(10) Patent No.: US 7,833,534 B2
(45) Date of Patent: Nov. 16, 2010

(54) COMPOUNDS AND METHODS FOR DIAGNOSIS AND TREATMENT OF LEISHMANIASIS

(75) Inventors: Yasuyuki Goto, Seattle, WA (US); Steven G. Reed, Bellevue, WA (US)

(73) Assignee: Infectious Disease Research Institute, Seattle, WA (US)

( * ) Notice: Subject to any disclaimer, the term of this patent is extended or adjusted under 35 U.S.C. 154(b) by 78 days.

(21) Appl. No.: 11/733,440

(22) Filed: Apr. 10, 2007

(65) Prior Publication Data

US 2007/0237794 A1    Oct. 11, 2007

Related U.S. Application Data

(60) Provisional application No. 60/791,226, filed on Apr. 10, 2006, provisional application No. 60/744,798, filed on Apr. 13, 2006.

(51) Int. Cl.
*A61K 39/02* (2006.01)
*A61K 49/00* (2006.01)
*A61N 63/00* (2006.01)

(52) U.S. Cl. .................. 424/234.1; 424/9.1; 424/9.2; 424/93.4; 424/93.6; 424/184.1; 424/204.1; 436/501; 530/300; 530/350; 536/23.7

(58) Field of Classification Search .............. 424/9.1, 424/9.2, 93, 184.1, 204.1, 234.1, 93.4, 93.6; 436/501; 530/300, 350; 536/23.7
See application file for complete search history.

(56) References Cited

U.S. PATENT DOCUMENTS

| 5,411,865 | A  | 5/1995  | Reed         |
|-----------|----|---------|--------------|
| 5,733,778 | A  | 3/1998  | Matlashewski |
| 5,756,662 | A  | 5/1998  | Reed         |
| 6,638,517 | B2 | 10/2003 | Reed         |

OTHER PUBLICATIONS

Burns,J.M., et al, PNAS, Jan. 1993, pp. 775-779, vol. 90.
Zhou X., et al., Journal of Immunological Methods, 1992, pp. 193, 153.
De Groot, A.S., et al, Vaccine, Aug. 2001, pp. 4385-4395, 19(31).
Burns, J.M., et al, PNAS, Feb. 1992, pp. 1239-1243, vol. 89.
Benson, G., Nucleic Acids Research, 1999, pp. 573-580, 27.

*Primary Examiner*—Rodney P. Swartz
(74) *Attorney, Agent, or Firm*—Graybeal Jackson LLP; Dylan O. Adams

(57) ABSTRACT

Compounds and methods are provided for diagnosing, preventing, treating and detecting leishmaniasis infection and stimulating immune responses in patients are disclosed. The compounds disclosed are include polypeptides and fusion proteins that contain at least one immunogenic portion of one or more *Leishmania* antigens, or a variant thereof. Additionally, methods of screening a screening library for tandem repeat proteins that have immunogenic properties are disclosed. Vaccines and pharmaceutical compositions comprising polynucleotides, polypeptides, fusion proteins and variants thereof that may be used for the prevention and therapy of leishmaniasis, as well as for the detection of Leishmaniasis infection are described.

17 Claims, 5 Drawing Sheets

SEQUENCE LISTING

<160> NUMBER OF SEQ ID NOS: 126

<210> SEQ ID NO 1
<211> LENGTH: 39
<212> TYPE: PRT
<213> ORGANISM: Leishmania infantum

<400> SEQUENCE: 1

Gln Gln Arg Leu Val Thr Ala Ala Gln Gln Arg Ala Glu Leu Glu Ala
1               5                   10                  15

Gln Val Ala Arg Leu Ala Ala Asp Arg Asp Glu Ala Arg Glu Gln Leu
            20                  25                  30

Ala Ala Asn Ala Glu Glu Leu
        35

<210> SEQ ID NO 2
<211> LENGTH: 38
<212> TYPE: PRT
<213> ORGANISM: Leishmania infantum

<400> SEQUENCE: 2

Asp Pro Ala Met Tyr Asn Thr Thr Lys Asp Ala Tyr Lys Lys Tyr
1               5                   10                  15

Asp Pro Asp Ala Tyr Arg Arg Glu Leu Pro Ala Asp Asp Gly Glu Gly
            20                  25                  30

Tyr Glu Lys Ala Pro Val
        35

<210> SEQ ID NO 3
<211> LENGTH: 76
<212> TYPE: PRT
<213> ORGANISM: Leishmania infantum

<400> SEQUENCE: 3

Met Gln Ile Phe Val Lys Thr Leu Thr Gly Lys Thr Ile Ala Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Glu Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 4
<211> LENGTH: 46
<212> TYPE: PRT
<213> ORGANISM: Leishmania infantum

<400> SEQUENCE: 4

Leu Arg His Gln Leu Ala Ala Gly Ala Asp Glu Gln Ala Gln Ala His
1               5                   10                  15

Glu Ala Leu Arg Ala Glu Leu Ala Ala Ala Gln Ser Glu Arg Asp Asn
            20                  25                  30

Ala Ala Gln Gln Ala Gln Arg His Ala Glu Glu Leu Glu Gln
        35                  40                  45

<210> SEQ ID NO 5
<211> LENGTH: 21
<212> TYPE: PRT
<213> ORGANISM: Leishmania infantum

<400> SEQUENCE: 5

Ala Ala Pro Ala Gly Glu Ala Gln Ala Ala Glu Glu Gln Glu Pro Ala
1               5                   10                  15

Gly Ala Asp Thr Tyr
            20

<210> SEQ ID NO 6
<211> LENGTH: 28
<212> TYPE: PRT
<213> ORGANISM: Leishmania infantum

<400> SEQUENCE: 6

Thr Pro Leu Arg Leu Glu Thr Ala Ser Gly Ala Asp Val Pro Thr Pro
1               5                   10                  15

Ser Arg Leu Glu Ala Ala Ser Gly Ala Asp Val Ala
            20                  25

<210> SEQ ID NO 7
<211> LENGTH: 56
<212> TYPE: PRT
<213> ORGANISM: Leishmania infantum

<400> SEQUENCE: 7

Gln Leu Glu Lys Ala His Ala Lys Leu Glu Lys Ser Ser Ala Ala Leu
1               5                   10                  15

```
Glu Gln Gln Val Ala Glu Trp Lys Thr Arg Ala Thr Ser Leu Asp Ala
            20                  25                  30

Glu Arg Gly Asp Val Ser Glu Arg Leu Val Arg Leu Glu Gly Glu His
        35                  40                  45

Ala Glu Leu Ala Arg Thr His Glu
    50                  55

<210> SEQ ID NO 8
<211> LENGTH: 105
<212> TYPE: PRT
<213> ORGANISM: Leishmania infantum

<400> SEQUENCE: 8

Ala Leu Arg Gly Gln Leu Glu Glu Ala Asn Ala Glu Lys Glu Arg Leu
1               5                   10                  15

Gln Ser Glu Leu Glu Glu Lys Gly Ser Glu Ala Glu Ala Ala Lys Glu
            20                  25                  30

Asp Ser Glu Ala Leu Arg Gly Gln Leu Glu Glu Ala Asn Ala Glu Lys
        35                  40                  45

Glu Arg Leu Gln Ser Glu Leu Glu Glu Lys Gly Ser Glu Ala Glu Ala
    50                  55                  60

Ala Lys Glu Asp Asn Glu Ala Leu Arg Gly Gln Leu Glu Glu Ala Asn
65                  70                  75                  80

Ala Glu Lys Glu Arg Leu Gln Ser Glu Leu Glu Glu Lys Gly Ser Glu
                85                  90                  95

Ala Glu Ala Ala Lys Glu Asp Ser Glu
            100                 105

<210> SEQ ID NO 9
<211> LENGTH: 161
<212> TYPE: PRT
<213> ORGANISM: Leishmania infantum

<400> SEQUENCE: 9

Ala Asn Ala Glu Lys Glu Arg Leu Gln Ser Glu Leu Glu Glu Lys Gly
1               5                   10                  15

Ser Glu Ala Glu Ala Ala Lys Glu Asp Ser Glu Ala Leu Arg Gly Gln
            20                  25                  30

Leu Glu Glu Thr Thr Gln Gln Leu Glu Glu Ala Asn Ala Glu Lys Glu
        35                  40                  45

Arg Leu Gln Ser Glu Leu Glu Glu Lys Gly Ser Glu Ala Glu Ala Ala
    50                  55                  60

Lys Glu Asp Ser Glu Ala Leu Arg Gly Gln Leu Glu Glu Thr Thr Gln
65                  70                  75                  80

Gln Leu Glu Glu Ala Asn Ala Glu Arg Glu Arg Leu Gln Ser Glu Leu
                85                  90                  95

Glu Glu Lys Gly Ser Glu Ala Glu Ala Ala Lys Glu Asp Asn Glu Ala
            100                 105                 110

Leu Arg Gly Gln Leu Glu Glu Thr Thr Gln Gln Leu Glu Glu Ala Asn
        115                 120                 125

Ala Glu Arg Glu Arg Leu Gln Ser Glu Leu Glu Glu Lys Gly Ser Glu
    130                 135                 140

Ala Glu Ala Ala Lys Glu Asp Asn Glu Ala Leu Arg Gly Gln Leu Glu
145                 150                 155                 160

Glu
```

-continued

```
<210> SEQ ID NO 10
<211> LENGTH: 24
<212> TYPE: PRT
<213> ORGANISM: Leishmania infantum

<400> SEQUENCE: 10

Ala Ser Glu Ala Ala Ser Glu Ser Glu Ala Gly Glu Glu Gly Leu Arg
1               5                   10                  15

Arg Pro Ala Ala Ala Ser Glu Glu
            20

<210> SEQ ID NO 11
<211> LENGTH: 35
<212> TYPE: PRT
<213> ORGANISM: Leishmania infantum

<400> SEQUENCE: 11

Met Gly Thr Pro Val Asp Glu Ala Glu Arg Ala Leu Glu Ser Ala Leu
1               5                   10                  15

Gln Gln Ala Gly Asp Ala Lys Glu Pro Ala Asp Arg Asp Ala Val Leu
            20                  25                  30

Glu Arg Ser
        35

<210> SEQ ID NO 12
<211> LENGTH: 35
<212> TYPE: PRT
<213> ORGANISM: Leishmania infantum

<400> SEQUENCE: 12

Gln Arg Ala Leu Glu Ser Ala Leu Gln Gln Ala Gly Asp Ala Lys Glu
1               5                   10                  15

Pro Ala Ser Arg Asp Ala Val Leu Glu Arg Ser Met Gly Thr Pro Val
            20                  25                  30

Asp Glu Thr
        35

<210> SEQ ID NO 13
<211> LENGTH: 14
<212> TYPE: PRT
<213> ORGANISM: Leishmania infantum

<400> SEQUENCE: 13

Thr Glu Glu Thr Leu Gln Glu Thr Ser Ala Lys Leu Ala Asp
1               5                   10

<210> SEQ ID NO 14
<211> LENGTH: 73
<212> TYPE: PRT
<213> ORGANISM: Leishmania infantum

<400> SEQUENCE: 14

Tyr Pro Phe Leu Arg Leu His Glu Glu Glu Gly Trp Ala Glu Ala Leu
1               5                   10                  15

Gly Ala Asp Glu Ala Phe Gln Gly Leu Ala Ala Glu Tyr Ala Asp Leu
            20                  25                  30

Val Cys Asp Ala Arg Lys Asn Ala Ala Ala Leu Arg Ala Val Glu Asp
        35                  40                  45

Ala Met Asn Glu Arg Gly Asp Ala Val Ala Ala Leu Arg Arg Ala
    50                  55                  60
```

```
Ala Ala Met Asp Glu Leu Ala Ser Arg
 65                  70
```

<210> SEQ ID NO 15
<211> LENGTH: 7
<212> TYPE: PRT
<213> ORGANISM: Leishmania infantum

<400> SEQUENCE: 15

```
His His His His His Arg His
1               5
```

<210> SEQ ID NO 16
<211> LENGTH: 27
<212> TYPE: PRT
<213> ORGANISM: Leishmania infantum

<400> SEQUENCE: 16

```
Ala Pro Gln Pro Ser Glu Ala Ala Pro Ala Ser Ala Val Glu Ala Leu
1               5                   10                  15

Pro Pro Thr Pro Ala Glu Cys Ala Ser Glu Ala
            20                  25
```

<210> SEQ ID NO 17
<211> LENGTH: 13
<212> TYPE: PRT
<213> ORGANISM: Leishmania infantum

<400> SEQUENCE: 17

```
Gln Ala Glu Asp Cys Asn Glu Ala Ala Pro Ala Glu Glu
1               5                   10
```

<210> SEQ ID NO 18
<211> LENGTH: 64
<212> TYPE: PRT
<213> ORGANISM: Leishmania infantum

<400> SEQUENCE: 18

```
Glu Ala Glu Leu Asp Ala Ala Asn Ala Glu Leu Gln Ala Thr Arg Glu
1               5                   10                  15

Ser Ala Ala Ala Ala Arg Pro Thr Arg Gly Asp Gly Asn Pro Phe Ala
            20                  25                  30

Asp Ala Glu Asp Pro Phe Gly Gly Ser Ser Arg Val Ala Ala Pro Cys
        35                  40                  45

Ala Asp Asp Gly Ala Leu Asp Ala Ala Arg Gln Arg Ile Ala Glu Leu
    50                  55                  60
```

<210> SEQ ID NO 19
<211> LENGTH: 61
<212> TYPE: PRT
<213> ORGANISM: Leishmania infantum

<400> SEQUENCE: 19

```
Gly Val Ala Ala Glu Ala Ala Gly Ala Leu Ala Gln Leu Ala Glu Asp
1               5                   10                  15

Arg Ala Ala Asp Met Ala Gln Ala Val Ser Ser Ala Glu Gly Gly Ser
            20                  25                  30

Arg Ala Ala Leu Glu Ala Thr Glu Ala Ala Glu Arg Ala Glu Gln Glu
        35                  40                  45

Arg Ala Cys Val Ala Ser Glu Glu Cys Ala Ala Arg Ala
    50                  55                  60
```

```
<210> SEQ ID NO 20
<211> LENGTH: 27
<212> TYPE: PRT
<213> ORGANISM: Leishmania infantum

<400> SEQUENCE: 20

Ala Pro Gln Pro Ser Glu Ala Ala Pro Val Ser Ala Val Glu Ala Leu
1               5                   10                  15

Pro Pro Thr Pro Ala Glu Cys Ala Ser Glu Ala
            20                  25

<210> SEQ ID NO 21
<211> LENGTH: 13
<212> TYPE: PRT
<213> ORGANISM: Leishmania infantum

<400> SEQUENCE: 21

Asp Val Asn Val His Asn Thr Gln Thr Lys Met Tyr Ile
1               5                   10

<210> SEQ ID NO 22
<211> LENGTH: 27
<212> TYPE: PRT
<213> ORGANISM: Leishmania infantum

<400> SEQUENCE: 22

Gln Pro Ser Glu Ala Ala Pro Ala Ser Ala Val Glu Ala Leu Pro Pro
1               5                   10                  15

Thr Pro Ala Glu Cys Ala Ser Asp Ala Val Pro
            20                  25

<210> SEQ ID NO 23
<211> LENGTH: 89
<212> TYPE: PRT
<213> ORGANISM: Leishmania infantum

<400> SEQUENCE: 23

Val Cys Leu His Ala Phe Arg Gly Cys Cys Arg Tyr Cys Val Gly Trp
1               5                   10                  15

Leu Gln Thr Pro Leu Phe Val Asp Tyr Ile Phe Leu Ser Phe Ala Leu
            20                  25                  30

Val Phe Tyr Ile Tyr Ser His Ser Phe Ser His Leu Pro Ile Tyr Leu
        35                  40                  45

Phe Phe Pro Pro Ala Ala Leu Pro Leu Pro His Ser Leu Gly Ala Cys
    50                  55                  60

Gly Gly Gly Ser Pro Leu Leu Ser Ile Pro Val Val Ala Ser Phe
65                  70                  75                  80

Gln Ile Val Phe Ser Lys Ile Lys Arg
                85

<210> SEQ ID NO 24
<211> LENGTH: 27
<212> TYPE: PRT
<213> ORGANISM: Leishmania infantum

<400> SEQUENCE: 24

Ala Pro Gln Pro Ser Glu Ala Ala Pro Val Ser Ala Val Glu Ala Leu
1               5                   10                  15

Pro Pro Thr Pro Ala Glu Cys Ala Ser Glu Ala
            20                  25
```

```
<210> SEQ ID NO 25
<211> LENGTH: 89
<212> TYPE: PRT
<213> ORGANISM: Leishmania infantum

<400> SEQUENCE: 25

Cys Arg Leu Val Ser Asn Cys Phe Phe Glu Ser Gln Ala Cys Val Phe
1               5                   10                  15

Ala Arg Leu Pro Trp Leu Leu Ser Leu Leu Arg Arg Leu Val Ala Asp
                20                  25                  30

Thr Ser Phe Arg Arg Leu Tyr Leu Ser Phe Leu Arg Pro Arg Leu Leu
            35                  40                  45

His Leu Leu Pro Phe Val Leu Ser Ser Pro Tyr Ile Phe Val Phe Pro
    50                  55                  60

Thr Arg Gly Ser Ser Ser Thr Ser Leu Pro Arg Cys Val Trp Trp Trp
65                  70                  75                  80

Phe Ala Ser Leu Val Asp Ser Cys Ser
                85

<210> SEQ ID NO 26
<211> LENGTH: 28
<212> TYPE: PRT
<213> ORGANISM: Leishmania infantum

<400> SEQUENCE: 26

Ala Asp Leu Arg Glu Gln Leu Arg Glu Ala Glu Glu Arg Ala Arg Asp
1               5                   10                  15

Val Glu Ala Gln Gln Cys Asp Arg Asp Ala Glu Val
                20                  25

<210> SEQ ID NO 27
<211> LENGTH: 22
<212> TYPE: PRT
<213> ORGANISM: Leishmania infantum

<400> SEQUENCE: 27

Ala Glu Ser Val Ala Thr Ile Ser Ile Arg Glu Glu Pro Ser Glu Gly
1               5                   10                  15

His Arg Asp Asp Lys Val
            20

<210> SEQ ID NO 28
<211> LENGTH: 123
<212> TYPE: PRT
<213> ORGANISM: Leishmania infantum

<400> SEQUENCE: 28

Ala Asp Val Pro Leu Ala Glu Glu His Glu Asp Gln Pro Glu Ala Tyr
1               5                   10                  15

Pro Glu Asp Ala Gln Trp Ala Gly Glu Ala Leu Met Thr Thr Glu Asp
                20                  25                  30

Ala Lys Pro Ala Glu Asp Glu Asp Lys Tyr Ser Glu Asp Gly Phe Phe
            35                  40                  45

Lys Asp Ser Ala Ala Asp Ser Ala Val Ala Glu Pro Gln Leu Tyr
    50                  55                  60

Asn Arg Leu Asp Ala Ala Ala His Asp Asp Ala Val Lys Ala Lys
65                  70                  75                  80

Ser Asp Val Ala Asp Asp Ala Tyr Asp Glu Asp Asn Phe Glu Asp Glu
                85                  90                  95
```

-continued

```
Leu Pro Ser Lys Lys Ser Ser Val Ala Ser Ser Ala Pro Arg Ser Pro
            100                 105                 110

Ala Ala Gly Ser Arg Lys Ser Asp Ala Ser Gly
        115                 120

<210> SEQ ID NO 29
<211> LENGTH: 16
<212> TYPE: PRT
<213> ORGANISM: Leishmania infantum

<400> SEQUENCE: 29

Ala Pro Gln Glu Ala Tyr Glu Gly Val Glu Ala Asp Arg Ala Ala
1               5                   10                  15

<210> SEQ ID NO 30
<211> LENGTH: 10
<212> TYPE: PRT
<213> ORGANISM: Leishmania infantum

<400> SEQUENCE: 30

Gln Gln Ala Glu Ala Glu Glu Ala Ala Arg
1               5                   10

<210> SEQ ID NO 31
<211> LENGTH: 10
<212> TYPE: PRT
<213> ORGANISM: Leishmania infantum

<400> SEQUENCE: 31

Ala Ala Arg Gln Gln Ala Glu Ala Glu Glu
1               5                   10

<210> SEQ ID NO 32
<211> LENGTH: 68
<212> TYPE: PRT
<213> ORGANISM: Leishmania infantum

<400> SEQUENCE: 32

Arg Ala His Asp Leu Ala Cys Asp Lys Lys Trp Ala Asp Arg Asp Arg
1               5                   10                  15

Val Leu Asp Pro Lys Pro Glu Gly Val Pro Leu Arg Cys Val Pro Leu
            20                  25                  30

Asp Glu Asp Ala Glu Phe Val Ala Leu Glu Asp Glu Trp Arg Gly Leu
        35                  40                  45

Leu Gln Asp Pro Gln Arg Asn Ser Met Pro Leu Lys Asp Leu Glu Arg
    50                  55                  60

Arg Met Asn Asp
65

<210> SEQ ID NO 33
<211> LENGTH: 105
<212> TYPE: PRT
<213> ORGANISM: Leishmania infantum

<400> SEQUENCE: 33

Glu Glu Leu Gln Arg Gln Arg Glu Glu Glu Lys Gln Arg Ile Glu
1               5                   10                  15

Met Val Arg Lys Gln Arg Glu Glu Ala Gln Lys Lys Arg Glu Glu Ile
            20                  25                  30

Gln Lys Gln Arg Glu Asp Glu Ile Lys Arg Arg Lys Ala Glu Ile Glu
        35                  40                  45
```

```
Ala Glu Arg Gln Lys Leu Lys Glu Leu Gln Glu Glu His Glu Arg Glu
        50                  55                  60

Gln Glu Glu Val Arg Gln Arg Val Ala Glu Lys Glu Ala Gln
65                  70                  75                  80

Lys Arg Ala Glu Lys Ala Glu Val Glu Gly Glu Phe Ala Ala
                85                  90                  95

Thr Arg Gln Arg Lys Gly Glu Leu
            100                 105

<210> SEQ ID NO 34
<211> LENGTH: 20
<212> TYPE: PRT
<213> ORGANISM: Leishmania infantum

<400> SEQUENCE: 34

Ala Ala Pro Phe Lys Ser Ala Phe Gly Ala Val Ser Ala Pro Asp Ala
1               5                   10                  15

Ala Lys Pro Ala
            20

<210> SEQ ID NO 35
<211> LENGTH: 8
<212> TYPE: PRT
<213> ORGANISM: Leishmania infantum

<400> SEQUENCE: 35

Ala Glu Glu Gln Ala Arg Arg Val
1               5

<210> SEQ ID NO 36
<211> LENGTH: 39
<212> TYPE: PRT
<213> ORGANISM: Leishmania infantum

<400> SEQUENCE: 36

Leu Glu Ala Ala Lys Ala Val Ala Asp Ala Arg Val Gln Glu Leu Glu
1               5                   10                  15

Ala Ala Ala Ala Ser Ser Ala Glu Val Ala Ser Arg Leu Ala Ala Glu
            20                  25                  30

His Ala Glu His Val Ala Gly
        35

<210> SEQ ID NO 37
<211> LENGTH: 25
<212> TYPE: PRT
<213> ORGANISM: Leishmania infantum

<400> SEQUENCE: 37

Ser Ser Ser Gly Ser Ala Gly Glu Val Ser Gly Ser Ser Ser Ser Ser
1               5                   10                  15

Thr Ala Thr Thr Ala Glu Pro Thr Pro
            20                  25

<210> SEQ ID NO 38
<211> LENGTH: 8
<212> TYPE: PRT
<213> ORGANISM: Leishmania infantum

<400> SEQUENCE: 38

Pro Thr Thr Thr Thr Thr Glu Ala
1               5
```

<210> SEQ ID NO 39
<211> LENGTH: 152
<212> TYPE: PRT
<213> ORGANISM: Leishmania infantum

<400> SEQUENCE: 39

Arg Gly Gly Tyr Gly Ser Met Met Glu Ala Asp Ser Ala Val Ala Pro
1               5                   10                  15

Asp Ala Ser Ala Ala Ser Arg Ser Asn Gly Gly Tyr Ser Val Gly Gly
            20                  25                  30

Arg Ser Glu Thr Ser Val Gln Ser Arg Gly Gly Tyr Gly Ser Met Met
        35                  40                  45

Glu Ala Asp Ser Ala Val Ala Pro Asp Ala Gly Ala Ala Ser Arg Ser
50                  55                  60

Asn Gly Gly Tyr Ser Leu Gly Gly Arg Gly Tyr Gly Ser Met Met
65                  70                  75                  80

Glu Ala Asp Ser Ala Val Ala Pro Asp Ala Gly Ala Ala Ser Arg Ser
                85                  90                  95

Asn Gly Gly Tyr Ser Val Gly Gly Arg Ser Glu Thr Ser Val Arg Ser
            100                 105                 110

Arg Gly Gly Tyr Gly Ser Met Met Glu Ala Asp Ser Ala Val Ala Pro
        115                 120                 125

Asp Ala Gly Ala Ala Ser Arg Ser Asn Gly Gly Tyr Ser Leu Gly Gly
    130                 135                 140

Arg Ser Glu Thr Ser Val Gln Ser
145                 150

<210> SEQ ID NO 40
<211> LENGTH: 10
<212> TYPE: PRT
<213> ORGANISM: Leishmania infantum

<400> SEQUENCE: 40

Thr Thr Thr Thr Thr Thr Glu Ala Pro Thr
1               5                   10

<210> SEQ ID NO 41
<211> LENGTH: 50
<212> TYPE: PRT
<213> ORGANISM: Leishmania infantum

<400> SEQUENCE: 41

Thr Ala Glu Arg Glu Gln His Glu Ser Arg Val Ala Glu Leu Gln Gln
1               5                   10                  15

Gln Leu Glu Thr Glu Arg Asp Arg Ala Ala Ser Gln Ser Thr Val
            20                  25                  30

Glu Glu Arg Glu Ser Val Leu Gln Gln Arg Leu Ala Glu Leu Arg Thr
        35                  40                  45

Ser Met
    50

<210> SEQ ID NO 42
<211> LENGTH: 10
<212> TYPE: PRT
<213> ORGANISM: Leishmania infantum

<400> SEQUENCE: 42

Glu Glu Gln Ala Arg Leu Ala Arg Glu Ala

-continued

```
1               5                   10
```

<210> SEQ ID NO 43
<211> LENGTH: 33
<212> TYPE: PRT
<213> ORGANISM: Leishmania infantum

<400> SEQUENCE: 43

Ala Ala Pro Lys Arg Pro Leu Thr Ala Glu Gln Ile Ala Ala Glu Arg
1               5                   10                  15

Ala Glu Leu Asp Arg Leu Glu Arg Glu Leu Leu Ala Ser Glu Ala
            20                  25                  30

Thr

<210> SEQ ID NO 44
<211> LENGTH: 148
<212> TYPE: PRT
<213> ORGANISM: Leishmania infantum

<400> SEQUENCE: 44

Glu Glu His Ala Pro Ala Leu Gln Arg Val Gly Thr Pro Val Glu Pro
1               5                   10                  15

Gln Pro Arg Leu Ala Val Thr Thr His Arg Val Arg Leu Asp Gly Asp
            20                  25                  30

Leu Trp Ala Arg Val Val Asp Glu Trp Pro Asp Leu Leu Lys Gln Glu
        35                  40                  45

Phe Thr Ser Asp Val Cys Asp Ala Thr Ala Leu Pro Arg Thr Ser Met
    50                  55                  60

Gln Arg Leu Val Leu Thr Ala Gly Ser Leu Val Ala Asp Phe Gln Leu
65                  70                  75                  80

Ser His Gly Gly Leu Ala Lys Arg Glu Leu Asn Lys Gln Leu Ala Ser
                85                  90                  95

Ser Pro Phe Thr Arg Thr Trp Ala Leu Tyr Glu Arg Val Ala Glu Thr
            100                 105                 110

Lys Glu Thr Pro Pro Thr Arg Ala Thr Pro Pro Ala Ala Leu Arg Ala
        115                 120                 125

Ser Glu Ser Phe Ala Ser Leu Asp Pro Val Glu Glu Ala Ala Val Leu
    130                 135                 140

Arg Ala Gln Gln
145

<210> SEQ ID NO 45
<211> LENGTH: 111
<212> TYPE: PRT
<213> ORGANISM: Leishmania infantum

<400> SEQUENCE: 45

Gly Ala Gly Gly Gly Arg Asp Thr Gly Arg Arg Ala Ala Glu Gly Ala
1               5                   10                  15

Gly Gly Arg Gly Glu Ala Glu Gly Arg Gln Pro Pro Ala Gly Gln Arg
            20                  25                  30

Gln Arg Ala Ala Gly His Arg Ala Gly Glu Gly Ala Gly Gly Gly Arg
        35                  40                  45

Glu Ala Gly Arg Arg Ser Arg Lys Gly Ala Gly Gly Gly Arg Asp Thr
    50                  55                  60

Gly Gly Glu Leu Gln Lys Ala Gln Glu Asp Gly Glu Arg Gln Lys Ala
65                  70                  75                  80

```
Asp Asn Arg Gln Leu Ala Ser Asp Asn Glu Arg Leu Ala Thr Glu Leu
            85                  90                  95

Glu Arg Ala Gln Glu Glu Ala Glu Arg Leu Ala Gly Asp Leu Glu
        100                 105                 110

<210> SEQ ID NO 46
<211> LENGTH: 83
<212> TYPE: PRT
<213> ORGANISM: Leishmania infantum

<400> SEQUENCE: 46

Arg Ala Glu Ala Glu Arg Leu Ala Lys Glu Val Ala Ala Phe Arg Ala
1               5                   10                  15

Arg Arg Asn Ala Ala Leu Glu Ala Arg Asp Ala Asp Gly Thr Leu Pro
            20                  25                  30

Val Pro Ala Arg Pro Val Pro Ala Gly Glu Ala Ala Glu Arg Ala Leu
        35                  40                  45

Glu Pro Gln Gln Ile Ala Asp Glu Pro Leu Tyr Ala Val Thr Leu Glu
    50                  55                  60

Glu Tyr Leu Gly Lys Asp Ala Ala Val Glu Gln Leu Ala Ala Glu Leu
65                  70                  75                  80

Glu Glu Gln

<210> SEQ ID NO 47
<211> LENGTH: 56
<212> TYPE: PRT
<213> ORGANISM: Leishmania infantum

<400> SEQUENCE: 47

Gln Glu Glu Ala Glu Arg Leu Ala Gly Asp Leu Glu Lys Ala Glu Glu
1               5                   10                  15

Glu Ala Glu Thr Leu Ala Gly Glu Leu Gln Lys Ala Gln Glu Asp Gly
            20                  25                  30

Glu Arg Gln Lys Ala Asp Asn Arg Gln Leu Ala Ser Asp Asn Glu Arg
        35                  40                  45

Leu Ala Thr Glu Leu Glu Arg Ala
    50                  55

<210> SEQ ID NO 48
<211> LENGTH: 15
<212> TYPE: PRT
<213> ORGANISM: Leishmania infantum

<400> SEQUENCE: 48

Pro Ser Ala Ser Ser Ser Ser Ala Pro Ser Ser Ser Ser Ser Ala
1               5                   10                  15

<210> SEQ ID NO 49
<211> LENGTH: 45
<212> TYPE: PRT
<213> ORGANISM: Leishmania infantum

<400> SEQUENCE: 49

Pro Ala Ala Ala Pro Arg Arg Arg Pro Arg Arg Leu Arg Arg Pro
1               5                   10                  15

Ala Ala Ala Pro Arg Arg Arg Arg Arg Arg Leu Arg Arg Pro Ala
            20                  25                  30

Ala Ala Pro Arg Arg Arg Pro Arg Arg Leu Arg Arg
        35                  40                  45
```

```
<210> SEQ ID NO 50
<211> LENGTH: 15
<212> TYPE: PRT
<213> ORGANISM: Leishmania infantum

<400> SEQUENCE: 50

Gln Gln Gln Leu Arg Ala Val Gly Val Leu Val Val Cys Ala Val
1               5                   10                  15

<210> SEQ ID NO 51
<211> LENGTH: 30
<212> TYPE: PRT
<213> ORGANISM: Leishmania infantum

<400> SEQUENCE: 51

Gln Gln Leu Arg Ala Val Gly Val Leu Val Val Cys Ala Val Gln Gln
1               5                   10                  15

Gln Leu Arg Ala Val Gly Val Leu Val Val Cys Thr Val Gln
            20                  25                  30

<210> SEQ ID NO 52
<211> LENGTH: 15
<212> TYPE: PRT
<213> ORGANISM: Leishmania infantum

<400> SEQUENCE: 52

Val Leu Val Val Cys Ala Val Gln Gln Gln Leu Arg Ala Val Gly
1               5                   10                  15

<210> SEQ ID NO 53
<211> LENGTH: 15
<212> TYPE: PRT
<213> ORGANISM: Leishmania infantum

<400> SEQUENCE: 53

Gln Leu Arg Ala Val Gly Val Leu Val Val Cys Ala Val Gln Gln
1               5                   10                  15

<210> SEQ ID NO 54
<211> LENGTH: 47
<212> TYPE: PRT
<213> ORGANISM: Leishmania infantum

<400> SEQUENCE: 54

Leu Arg Ala Ile Ala Gln Ala Leu Gly Val Pro Pro Asp Ala Tyr Ala
1               5                   10                  15

Gly Glu Arg Asp Gly Glu Cys Val Pro Thr Thr Gly Gln Leu Ala Glu
            20                  25                  30

Arg Ala Gly Ala Val Val Ser Ala Arg Ala Glu Glu Thr Ala Gly
        35                  40                  45

<210> SEQ ID NO 55
<211> LENGTH: 42
<212> TYPE: PRT
<213> ORGANISM: Leishmania infantum

<400> SEQUENCE: 55

Ala Glu Gln Glu Ala Glu Met Val Ala Leu Arg Gln Leu Leu Ala Glu
1               5                   10                  15

Ala Gln Arg Glu Ala Gln Ala Ala Gly Ala Arg Gln Arg Asp Ser Gly
            20                  25                  30

Ala Ala Val Gln Ala Leu Arg Asp Gln Met
```

<210> SEQ ID NO 56
<211> LENGTH: 55
<212> TYPE: PRT
<213> ORGANISM: Leishmania infantum

<400> SEQUENCE: 56

Lys Pro Ser Pro Lys Gln Ala Pro Lys Lys Ala Pro Ile Ala Asp Ser
1               5                   10                  15

Asp Ser Asp Asp Asp Glu Pro Val Arg Lys Pro Val Leu Ala Lys Lys
            20                  25                  30

Pro Val Ala Asp Ser Ser Ser Asp Glu Glu Glu Ala Pro Lys Lys Pro
        35                  40                  45

Ala Ala Lys Arg Pro Ser Pro
    50                  55

<210> SEQ ID NO 57
<211> LENGTH: 24
<212> TYPE: PRT
<213> ORGANISM: Leishmania infantum

<400> SEQUENCE: 57

Ser Ser Ser Asp Val Thr Thr Ala Ser Ser Glu Gly Thr Thr Ala
1               5                   10                  15

Ser Ser Ser Glu Gly Thr Thr Ala
            20

<210> SEQ ID NO 58
<211> LENGTH: 92
<212> TYPE: PRT
<213> ORGANISM: Leishmania infantum

<400> SEQUENCE: 58

Glu Glu Arg Leu Glu Ala Ala Ser Ala Glu Gln Gln Gln Leu Gln Ala
1               5                   10                  15

Asp Arg Asp Ala Lys Leu Arg Ala Ala Asp Glu Arg Leu Ala Gln Thr
            20                  25                  30

Ala Ala Ala Arg Gln Glu Leu Cys Asp Ser Val Ala Asp Ala Leu Ala
        35                  40                  45

Ala Leu Gly Ala Asp Ala Pro Ala Ser Pro Ser Val Ala Glu Ala Ile
    50                  55                  60

Ala Arg Ala Ala Ala Asp Ala Ala Glu Arg Glu Arg Ala Leu Arg Ala
65                  70                  75                  80

Glu Val Ala Ala Ala Glu Glu Arg Leu Gln Ala Met
                85                  90

<210> SEQ ID NO 59
<211> LENGTH: 10
<212> TYPE: PRT
<213> ORGANISM: Leishmania infantum

<400> SEQUENCE: 59

Val Cys Val Cys Val Cys Val Cys Val Cys
1               5                   10

<210> SEQ ID NO 60
<211> LENGTH: 117
<212> TYPE: DNA
<213> ORGANISM: Leishmania infantum

```
<400> SEQUENCE: 60
cagcagcgcc tggtcacggc cgcgcagcag cgcgccgagc tggaggcaca ggtggcacgg       60
ctggccgcgg accgcgacga ggcgcgcgag cagctggccg cgaacgccga ggagctg        117

<210> SEQ ID NO 61
<211> LENGTH: 114
<212> TYPE: DNA
<213> ORGANISM: Leishmania infantum

<400> SEQUENCE: 61
gaccccgcca tgtacaacac gaccaccaag gacgcctaca agaagtacga ccccgacgcg       60
tacaggcgcg agctgccggc ggacgacggc gagggctacg agaaggcgcc cgtg            114

<210> SEQ ID NO 62
<211> LENGTH: 228
<212> TYPE: DNA
<213> ORGANISM: Leishmania infantum

<400> SEQUENCE: 62
atgcagatct tcgtgaagac gctgaccggc aagacgatcg cgctggaggt ggagccgagc       60
gacacgatcg agaacgtgaa ggcgaagatc caggacaagg agggcatccc gccggaccag      120
cagcgcctga tcttcgccgg caagcagctg gaggagggcc gcacgctctc ggactacaac      180
atccagaagg agtccacgct gcacctggtg ctgcgcctgc gcggcggc                    228

<210> SEQ ID NO 63
<211> LENGTH: 138
<212> TYPE: DNA
<213> ORGANISM: Leishmania infantum

<400> SEQUENCE: 63
ctccgccacc agctggccgc cggcgcggac gagcaggcac aggcccacga ggccctccgc       60
gctgagctgg cggcggcgca gagcgagcgc gacaacgccg cgcagcaggc gcagcggcac      120
gcagaggagc tggagcag                                                     138

<210> SEQ ID NO 64
<211> LENGTH: 63
<212> TYPE: DNA
<213> ORGANISM: Leishmania infantum

<400> SEQUENCE: 64
gccgcgccag ctggggaggc gcaggccgcg gaagagcagg agcctgctgg cgccgatacc       60
tac                                                                      63

<210> SEQ ID NO 65
<211> LENGTH: 84
<212> TYPE: DNA
<213> ORGANISM: Leishmania infantum

<400> SEQUENCE: 65
acaccgctgc gtctcgagac agcctccggc gccgacgtgc cgactccctc gcgtctcgag       60
gcagcctccg gcgcagatgt cgcg                                              84

<210> SEQ ID NO 66
<211> LENGTH: 168
<212> TYPE: DNA
<213> ORGANISM: Leishmania infantum

<400> SEQUENCE: 66
```

```
cagctggaga aggcgcatgc gaagctggag aagtcgagtg ccgctctgga gcagcaggtg    60
gcggagtgga agacccgcgc cacgagcctg gacgctgagc gcggcgacgt gtcggagcgc   120
cttgtgcggc tggagggcga gcacgcggag ctggccagga cgcacgag                168

<210> SEQ ID NO 67
<211> LENGTH: 315
<212> TYPE: DNA
<213> ORGANISM: Leishmania infantum

<400> SEQUENCE: 67
gcgctgcgcg gccagctgga ggaggcgaac gcggagaagg agcgcctgca gagcgagctg    60
gaggagaagg gctcggaggc cgaggccgcc aaggaggaca gcgaggcgct gcgcggccag   120
ctggaggagg cgaacgcgga gaaggagcgt ctgcagagcg agctggagga aagggctcg   180 gaggcggagc ccgccaagga ggacaacgag gcgctgcgcg gccagctgga ggaggcgaac   240
gcggagaagg agcgtctgca gagcgagctg gaggagaagg gctcggaggc cgaggccgcc   300
aaggaggaca gcgag                                                    315

<210> SEQ ID NO 68
<211> LENGTH: 483
<212> TYPE: DNA
<213> ORGANISM: Leishmania infantum

<400> SEQUENCE: 68
gcgaacgcgg agaaggagcg tctgcagagc gagctggagg agaagggctc ggaggccgag    60
gccgccaagg aggacagcga ggcgctgcgc ggccagctgg aggagacgac ccagcagctg   120
gaggaggcga acgcggagaa ggagcgcctg cagagcgagc tggaggagaa gggctcggag   180
gcggaggccg ccaaggagga cagcgaggcg ctgcgcggcc agctggagga gacgacccag   240
cagctggagg aggcgaacgc ggagagggag cgtctgcaga gcgagctgga ggagaagggc   300
tcggaggccg aggccgccaa ggaggacaac gaggcgctgc gcggccagct ggaggagacg   360
acccagcagc tggaggaggc gaacgcggag agggagcgtc tgcagagcga gctggaggag   420
aagggctcgg aggccgaggc cgccaaggag gacaacgagg cgctgcgcgg ccagctggag   480
gag                                                                 483

<210> SEQ ID NO 69
<211> LENGTH: 72
<212> TYPE: DNA
<213> ORGANISM: Leishmania infantum

<400> SEQUENCE: 69
gcgtcggaag ccgcttcgga atccgaggcg ggggaagagg gtctgcgccg gcctgcggcg    60
gcgtcggaag ag                                                        72

<210> SEQ ID NO 70
<211> LENGTH: 105
<212> TYPE: DNA
<213> ORGANISM: Leishmania infantum

<400> SEQUENCE: 70
atgggcacgc ccgtcgacga ggcggagcgg gcgctggaga gcgctctgca gcaagccggc    60
gatgcgaagg agcccgccga ccgcgacgcc gtgctggagc ggtcg                   105

<210> SEQ ID NO 71
```

```
<211> LENGTH: 105
<212> TYPE: DNA
<213> ORGANISM: Leishmania infantum

<400> SEQUENCE: 71
cagcgggcgc tggagagcgc tctgcagcaa gccggcgatg cgaaggagcc cgccagccgc      60
gacgccgtgc tggagcggtc gatgggcacg cccgtcgacg agacg                    105

<210> SEQ ID NO 72
<211> LENGTH: 42
<212> TYPE: DNA
<213> ORGANISM: Leishmania infantum

<400> SEQUENCE: 72
accgaggaga cgctgcagga gacgtccgcc aagctcgccg ac                        42

<210> SEQ ID NO 73
<211> LENGTH: 219
<212> TYPE: DNA
<213> ORGANISM: Leishmania infantum

<400> SEQUENCE: 73
tacccgttcc tacggctgca cgaggaggag gggtgggcgg aagcgcttgg ggcggacgag      60
gcgttccagg gtcttgctgc ggagtacgcg gacctggtgt gcgatgcgag gaagaacgcc     120
gccgcgctgc gcgctgtgga ggacgcgatg aacgagcgcg gcgacgccgt tgcggccgcg     180
ctgcggcgcg ctgctgcgat ggacgagctg gcgtcgcgc                           219

<210> SEQ ID NO 74
<211> LENGTH: 21
<212> TYPE: DNA
<213> ORGANISM: Leishmania infantum

<400> SEQUENCE: 74
caccaccacc accaccgaca c                                               21

<210> SEQ ID NO 75
<211> LENGTH: 30
<212> TYPE: DNA
<213> ORGANISM: Leishmania infantum

<400> SEQUENCE: 75
gtgtgcgtgt gcgtgtgcgt gtgcgtgtgc                                      30

<210> SEQ ID NO 76
<211> LENGTH: 81
<212> TYPE: DNA
<213> ORGANISM: Leishmania infantum

<400> SEQUENCE: 76
gcgccccagc cgagcgaggc ggcgccggcg tctgcagtgg aggctctgcc tccgacgcct      60
gccgagtgcg catctgaggc g                                               81

<210> SEQ ID NO 77
<211> LENGTH: 39
<212> TYPE: DNA
<213> ORGANISM: Leishmania infantum

<400> SEQUENCE: 77
caggctgagg attgcaacga ggccgcaccg gcagaggag                            39
```

<210> SEQ ID NO 78
<211> LENGTH: 192
<212> TYPE: DNA
<213> ORGANISM: Leishmania infantum

<400> SEQUENCE: 78
gaggcggagc tggatgcggc caatgctgag ctgcaggcta cccgcgagag tgccgctgct    60
gcgcggccca cacgcggtga cgggaacccg ttcgccgacg ccgaggaccc gttcggcggc   120
tcgtcgcgcg tcgctgcacc gtgtgcggac gacggggcgc tggatgctgc ccgccagagg   180
atcgcggagc tg                                                       192

<210> SEQ ID NO 79
<211> LENGTH: 183
<212> TYPE: DNA
<213> ORGANISM: Leishmania infantum

<400> SEQUENCE: 79
ggcgttgctg ccgaggcggc gggcgcgctg gcgcagctgg cggaggaccg cgccgcggac    60
atggcgcagg ccgtgtcgag cgccgaggga ggcagccgcg ccgcccttga ggcaaccgag   120
gccgccgagc gcgccgagca ggagcgcgct tgcgttgcgt cggaggagtg cgctgcgcgc   180
gcc                                                                 183

<210> SEQ ID NO 80
<211> LENGTH: 81
<212> TYPE: DNA
<213> ORGANISM: Leishmania infantum

<400> SEQUENCE: 80
gcgccccagc cgagcgaggc ggcgccggtg tctgcagtgg aggctctgcc tccgacgcct    60
gccgagtgcg catctgaggc g                                             81

<210> SEQ ID NO 81
<211> LENGTH: 39
<212> TYPE: DNA
<213> ORGANISM: Leishmania infantum

<400> SEQUENCE: 81
gacgttaatg tacacaacac acaaacaaag atgtatata                          39

<210> SEQ ID NO 82
<211> LENGTH: 81
<212> TYPE: DNA
<213> ORGANISM: Leishmania infantum

<400> SEQUENCE: 82
cagccgagcg aggcggcgcc ggcgtctgca gtggaggctc tgcctccgac gcctgccgag    60
tgcgcatccg acgccgtgcc a                                             81

<210> SEQ ID NO 83
<211> LENGTH: 267
<212> TYPE: DNA
<213> ORGANISM: Leishmania infantum

<400> SEQUENCE: 83
gtgtgtttgc acgccttccg tggttgctgt cgttactgcg tcggttggtt gcagacacct    60
cttttcgtcg actatatctt tctttctttc gccctcgtct tttacatcta ctcccattcg   120
ttctctcatc tccctatata tttgtttttc ccacccgcgg ctcttcctct acctcactcc   180

```
ctcggtgcgt gtggtggtgg ttcgcctctc ttgtcgattc ctgtagttgt cgcctcgttt    240
caaattgttt tttcgaaaat caagcgt                                        267

<210> SEQ ID NO 84
<211> LENGTH: 81
<212> TYPE: DNA
<213> ORGANISM: Leishmania infantum

<400> SEQUENCE: 84
gcgccccagc cgagcgaggc ggcgccggtg tctgcagtgg aggctctgcc tccgacgcct    60
gccgagtgcg catctgaggc g                                              81

<210> SEQ ID NO 85
<211> LENGTH: 267
<212> TYPE: DNA
<213> ORGANISM: Leishmania infantum

<400> SEQUENCE: 85
tgtcgcctcg tttcaaattg ttttttcgaa agtcaagcgt gtgtgtttgc acgccttccg    60
tggttgctgt cgttactgcg tcggttggtt gcagacacct cttttcgtcg actatatctt    120
tctttccttc gccctcgtct tttacatcta ctcccattcg ttctctcatc tccctatata    180 tttgttttc ccaccgcgg ctcttcctct acctcactcc ctcggtgcgt gtggtggtgg      240
ttcgcctctc ttgtcgattc ctgtagt                                        267

<210> SEQ ID NO 86
<211> LENGTH: 84
<212> TYPE: DNA
<213> ORGANISM: Leishmania infantum

<400> SEQUENCE: 86
gctgacctga gggagcagct gcgtgaggcg gaggagcgcg cgagggacgt ggaggcgcag    60
cagtgcgaca gggacgccga ggtg                                           84

<210> SEQ ID NO 87
<211> LENGTH: 66
<212> TYPE: DNA
<213> ORGANISM: Leishmania infantum

<400> SEQUENCE: 87
gccgagagtg tcgccaccat ctccatacgg gaggagccca gcgaaggcca ccgggacgac    60
aaggta                                                               66

<210> SEQ ID NO 88
<211> LENGTH: 369
<212> TYPE: DNA
<213> ORGANISM: Leishmania infantum

<400> SEQUENCE: 88
gccgatgtcc cgctggctga agagcacgag gaccagccgg aagcctatcc agaggatgcg    60
cagtgggctg gagaggcttt gatgaccacc gaggatgcga agccagcgga ggacgaggac    120
aagtacagcg aggacggctt cttcaaggat agcgccgcgg acagtgccgt cgcggcggaa    180
ccgcagctat acaatcggct ggatgccgcc gcccacgacg acgacgctgt gaaggccaag    240
agcgacgtag ccgacgacgc gtacgacgag gacaacttcg aggatgaact gccctccaag    300
aagtcgtcgg tggcctcgtc cgcgccgcga tcgccggccg cggggtcgag gaagagcgac    360
gcctcgggc                                                            369
```

<210> SEQ ID NO 89
<211> LENGTH: 48
<212> TYPE: DNA
<213> ORGANISM: Leishmania infantum

<400> SEQUENCE: 89
gctccgcagg aggcgtacga gggcgtggag gaggctgacc gcgctgcc         48

<210> SEQ ID NO 90
<211> LENGTH: 30
<212> TYPE: DNA
<213> ORGANISM: Leishmania infantum

<400> SEQUENCE: 90
cagcaggccg aggcggagga ggctgcccgc                              30

<210> SEQ ID NO 91
<211> LENGTH: 30
<212> TYPE: DNA
<213> ORGANISM: Leishmania infantum

<400> SEQUENCE: 91
gctgcccgcc agcaggccga ggcggaggag                              30

<210> SEQ ID NO 92
<211> LENGTH: 204
<212> TYPE: DNA
<213> ORGANISM: Leishmania infantum

<400> SEQUENCE: 92
cgcgcgcacg accttgcgtg cgacaagaag tgggcggacc gcgacagggt gctggacccg    60
aagccggagg gcgtgccgct gcgctgcgtc ccgctggacg aggacgcgga gttcgtggcg   120
ctggaggacg agtggcgcgg cctgctgcag gaccccacag gcaacagcat gccgctgaag   180
gacctggaga ggaggatgaa cgac                                         204

<210> SEQ ID NO 93
<211> LENGTH: 315
<212> TYPE: DNA
<213> ORGANISM: Leishmania infantum

<400> SEQUENCE: 93
gaggagctgc agcgccagcg cgaggaggag gagaagcagc gcatcgagat ggtgcgcaag    60
cagcgtgagg aggcccaaaa gaagcgggag gagatccaga agcagcgcga ggatgagatc   120
aagcgccgca aggctgagat cgaagcagag aggcagaagc tgaaggagct gcaggaggag   180
cacgagaggg agcaggagga ggtccgccag cgtcgcgtcg cggaggagaa ggaggcacag   240
aagagggccg agaagaaggc cgaggaggtc gagggcgagt tcgctgcgac gcgccggcag   300
aggaaggggg agttg                                                  315

<210> SEQ ID NO 94
<211> LENGTH: 60
<212> TYPE: DNA
<213> ORGANISM: Leishmania infantum

<400> SEQUENCE: 94
gctgcgccgt tcaagagcgc ctttggtgcc gtgtctgcac cggatgcggc caagcctgct    60

<210> SEQ ID NO 95

<211> LENGTH: 24
<212> TYPE: DNA
<213> ORGANISM: Leishmania infantum

<400> SEQUENCE: 95
gctgaggagc aggcgcgtcg cgtg                                           24

<210> SEQ ID NO 96
<211> LENGTH: 117
<212> TYPE: DNA
<213> ORGANISM: Leishmania infantum

<400> SEQUENCE: 96
ctggaggccg cgaaggctgt ggctgacgcg agggtgcagg agctggaggc ggctgccgcg    60
tcgagcgccg aggtggcgag caggctggcc gccgagcacg ctgagcacgt cgccggg      117

<210> SEQ ID NO 97
<211> LENGTH: 75
<212> TYPE: DNA
<213> ORGANISM: Leishmania infantum

<400> SEQUENCE: 97
agcagctccg gctcggccgg cgaggtgtcc gggtcgtcga gctcgagcac cgccacgacc    60
gcagagccga ctccg                                                     75

<210> SEQ ID NO 98
<211> LENGTH: 24
<212> TYPE: DNA
<213> ORGANISM: Leishmania infantum

<400> SEQUENCE: 98
ccgacgacca cgacgaccga ggca                                           24

<210> SEQ ID NO 99
<211> LENGTH: 456
<212> TYPE: DNA
<213> ORGANISM: Leishmania infantum

<400> SEQUENCE: 99
cgcggcgggt acggcagcat gatggaggcc gacagcgctg tggccccaga cgcgagcgct    60
gcgtcgcgtt cgaatggcgg gtacagcgtt ggcgggcgca gcgagacgag cgtgcaatcg   120
cgcggcgggt acggcagcat gatggaggcc gacagcgctg tggccccaga cgcgggcgct   180
gcgtcgcgtt cgaatggcgg gtacagcctt ggcgggcgcg gcgggtacgg cagcatgatg   240
gaggccgaca cgctgtggc cccagacgcg ggcgctgcgt cgcgttcgaa tggcgggtac    300
agcgttggcg ggcgcagcga gacgagcgtg cggtcgcgcg gcgggtacgg cagcatgatg   360
gaggccgaca cgctgtggc cccagacgcg ggcgctgcgt cgcgttcgaa tggcgggtac    420
agccttggcg ggcgcagcga gacgagcgtg caatcg                             456

<210> SEQ ID NO 100
<211> LENGTH: 30
<212> TYPE: DNA
<213> ORGANISM: Leishmania infantum

<400> SEQUENCE: 100
acaacgacca cgacgacaga ggcaccaacg                                     30

<210> SEQ ID NO 101
<211> LENGTH: 150

```
<212> TYPE: DNA
<213> ORGANISM: Leishmania infantum

<400> SEQUENCE: 101
acagcggagc gcgagcagca cgagagccgg gtggcggagc tgcagcagca gctagagacg      60
gagcgcgacc gcgcggctgc cagccagtct actgtggagg agcgcgagtc tgtgttgcag     120
cagcgcctcg ccgagctgcg caccagtatg                                      150

<210> SEQ ID NO 102
<211> LENGTH: 30
<212> TYPE: DNA
<213> ORGANISM: Leishmania infantum

<400> SEQUENCE: 102
gaggagcagg cacggctcgc ccgtgaggcg                                       30

<210> SEQ ID NO 103
<211> LENGTH: 99
<212> TYPE: DNA
<213> ORGANISM: Leishmania infantum

<400> SEQUENCE: 103
gcggccccga agcgcccgct cacggcggag cagattgcgg ctgagcgcgc tgagctggac      60
cggctggagc gcgaggagct gctggcctct gaggccacg                             99

<210> SEQ ID NO 104
<211> LENGTH: 444
<212> TYPE: DNA
<213> ORGANISM: Leishmania infantum

<400> SEQUENCE: 104
gaggagcatg cgccagcgct gcagcgcgtc ggcacgccgg tggagccgca gccgcgcctc      60
gcggtcacga cacaccgggt tcgcctggac ggcgatttgt gggcgcgtgt cgtcgacgag     120
tggccggacc tgctcaagca ggagttcaca agcgacgtgt gcgatgccac ggcgctgccg     180
cggacgtcga tgcagcggct ggtgctcaca gccggcagcc tcgtcgccga cttccagctc     240
tcgcacggag gcctcgcgaa gagggagctg aacaagcagc ttgccagctc gcccttcacc     300
cgcacctggg cactgtacga gcgcgtcgcc gagacgaaag agacgccgcc cacccgcgcc     360
acgccgccgg ctgcccttcg cgcctcggag agcttcgcgt cgctggaccc ggtggaggag     420
gccgcagtgc tgcgtgcgca gcag                                            444

<210> SEQ ID NO 105
<211> LENGTH: 335
<212> TYPE: DNA
<213> ORGANISM: Leishmania infantum

<400> SEQUENCE: 105
ggcgcaggag gaggccgaga cactggccgg cgagctgcag aaggcgcagg aggacgggga      60
gaggcagagg gccgacaacc gccagctggc cagcgacaac gagcggctgg ccaccgagct     120
ggagagggcg caggaggagg ccgagaggct ggccggcgat ctcgaaaagg cgcaggagga     180
ggccgagaca ctggcggcga gctgcagaag gcgcaggagg acggggagag gcagaaggcc     240
gacaaccgcc agctggccag cgacaacgag cggctggcca ccgagctgga gagggcgcag     300
gaggaggccg agaggctggc cggcgatctc gaaaa                                335

<210> SEQ ID NO 106
```

```
<211> LENGTH: 249
<212> TYPE: DNA
<213> ORGANISM: Leishmania infantum

<400> SEQUENCE: 106
agggcggagg cggagaggct tgcgaaggag gtggccgcct tccgcgcgag gcgcaacgcg      60
gcgctggagg cccgcgacgc ggacggcacg ctgcccgtgc cggcaaggcc tgtgcccgcg     120
ggcgaggcgg cggagcgcgc gctggagccg cagcagatcg ccgacgagcc gctgtacgct     180
gtgacgctgg aggagtacct gggcaaggac gcggccgtgg agcagctggc ggcggagctg     240
gaggagcag                                                             249

<210> SEQ ID NO 107
<211> LENGTH: 168
<212> TYPE: DNA
<213> ORGANISM: Leishmania infantum

<400> SEQUENCE: 107
caggaggagg ccgagaggct ggccggcgat ctcgaaaagg cagaggagga ggccgagaca      60
ctggcgggcg agctgcagaa ggcgcaggag gacggggaga ggcagaaggc cgacaaccgc     120
cagctggcca gcgacaacga gcggctggcc accgagctgg agagggcg                  168

<210> SEQ ID NO 108
<211> LENGTH: 45
<212> TYPE: DNA
<213> ORGANISM: Leishmania infantum

<400> SEQUENCE: 108
ccgtcggcgt cgtcgtcgtc tgcgccgtcc agcagcagct ccgcg                      45

<210> SEQ ID NO 109
<211> LENGTH: 135
<212> TYPE: DNA
<213> ORGANISM: Leishmania infantum

<400> SEQUENCE: 109
ccagcagcag ctccgcgccg tcggcgtcct cgtcgtctgc gccgtccagc agcagctccg      60
cgccgtcggc gtcgtcgtcg tctgcgccgt ccagcagcag ctccgcgccg tcggcgtcct     120
cgtcgtctgc gccgt                                                     135

<210> SEQ ID NO 110
<211> LENGTH: 45
<212> TYPE: DNA
<213> ORGANISM: Leishmania infantum

<400> SEQUENCE: 110
cagcagcagc tccgcgccgt cggcgtcctc gtcgtctgcg ccgtc                      45

<210> SEQ ID NO 111
<211> LENGTH: 90
<212> TYPE: DNA
<213> ORGANISM: Leishmania infantum

<400> SEQUENCE: 111
cagcagctcc gcgccgtcgg cgtcctcgtc gtctgcgccg tccagcagca gctccgcgcc      60
gtcggcgtcc tcgtcgtctg caccgtccag                                       90

<210> SEQ ID NO 112
<211> LENGTH: 45
```

```
<212> TYPE: DNA
<213> ORGANISM: Leishmania infantum

<400> SEQUENCE: 112
gtcctcgtcg tctgcgccgt ccagcagcag ctccgcgccg tcggc            45

<210> SEQ ID NO 113
<211> LENGTH: 45
<212> TYPE: DNA
<213> ORGANISM: Leishmania infantum

<400> SEQUENCE: 113
cagctccgcg ccgtcggcgt cctcgtcgtc tgcgccgtcc agcag            45

<210> SEQ ID NO 114
<211> LENGTH: 141
<212> TYPE: DNA
<213> ORGANISM: Leishmania infantum

<400> SEQUENCE: 114
ctgcgcgcca tcgcccaggc cctcggcgtg ccgccggacg cgtacgctgg cgagcgggac      60
ggcgagtgcg tgccaacaac cggacagcta gcggagcgcg ctggcgctgt ggtgagcgcc     120
cgcgctgagg agacggcggg g                                              141

<210> SEQ ID NO 115
<211> LENGTH: 126
<212> TYPE: DNA
<213> ORGANISM: Leishmania infantum

<400> SEQUENCE: 115
gcggagcagg aggcggagat ggttgcgctc cgccagctgc tggctgaggc acagcgcgag      60
gcacaggccg ccggcgcaag acagcgcgac agtggcgccg ctgtgcaggc gctgcgcgac     120
cagatg                                                               126

<210> SEQ ID NO 116
<211> LENGTH: 165
<212> TYPE: DNA
<213> ORGANISM: Leishmania infantum

<400> SEQUENCE: 116
aagccttcgc caaagcaggc ccccaagaag gcccccatcg ccgacagcga cagcgacgac      60
gacgagcctg ttcgcaagcc ggtgctagcc aaaaagcctg tggcggactc gagctctgac     120
gaggaggagg ctccgaaaaa gccggcggcg aagcgcccct tctccg                   165

<210> SEQ ID NO 117
<211> LENGTH: 72
<212> TYPE: DNA
<213> ORGANISM: Leishmania infantum

<400> SEQUENCE: 117
agcagcagcg acgttaccac cgccagcagc agcgagggca ccaccgccag cagcagcgag      60
ggcaccaccg cc                                                         72

<210> SEQ ID NO 118
<211> LENGTH: 276
<212> TYPE: DNA
<213> ORGANISM: Leishmania infantum

<400> SEQUENCE: 118
```

```
gaggagcgcc tggaggcggc gagcgccgag cagcagcagc tgcaggcgga ccgcgacgcg      60
aagctgcgtg ccgcggacga gcggctggcg cagacggcgg ctgcgcgcca ggagctgtgc     120
gacagcgttg ccgacgcgct tgctgcgttg ggtgcggacg cgccggcgtc gccgtctgtc     180
gcggaggcga ttgcgcgcgc ggccgccgat gccgcggagc gcgagcgtgc actgcgcgcc     240
gaggtcgccg cggcggagga gcgcctgcag gcgatg                               276
```

<210> SEQ ID NO 119
<211> LENGTH: 39
<212> TYPE: PRT
<213> ORGANISM: Leishmania infantum

<400> SEQUENCE: 119

Leu Glu Gln Gln Leu Arg Asp Ser Glu Arg Ala Ala Glu Leu Ala
1               5                   10                  15

Ser Gln Leu Glu Ala Thr Ala Ala Ala Lys Met Ser Ala Glu Gln Asp
            20                  25                  30

Arg Glu Asn Thr Arg Ala Ala
        35

<210> SEQ ID NO 120
<211> LENGTH: 14
<212> TYPE: PRT
<213> ORGANISM: Leishmania infantum

<400> SEQUENCE: 120

Lys Glu Asp Gly Arg Thr Gln Lys Asn Asp Gly Asp Gly Pro
1               5                   10

<210> SEQ ID NO 121
<211> LENGTH: 10
<212> TYPE: PRT
<213> ORGANISM: Leishmania infantum

<400> SEQUENCE: 121

Val Gly Pro Gln Ser Val Gly Pro Leu Ser
1               5                   10

<210> SEQ ID NO 122
<211> LENGTH: 63
<212> TYPE: DNA
<213> ORGANISM: Leishmania infantum

<400> SEQUENCE: 122

```
caattacata tgtacccgtt cctacggctg caattaggat ccctagcgcg acgccagctc      60
gtc                                                                    63
```

<210> SEQ ID NO 123
<211> LENGTH: 63
<212> TYPE: DNA
<213> ORGANISM: Leishmania infantum

<400> SEQUENCE: 123

```
caattacata tggctgacct gagggagcag caattaggat ccctacacct cggcgtccct      60
gtc                                                                    63
```

<210> SEQ ID NO 124
<211> LENGTH: 57
<212> TYPE: DNA
<213> ORGANISM: Leishmania infantum

```
-continued

<400> SEQUENCE: 124
caattacata tgagcgctgc accgtcccaa ttagaattcc tacgcaagtc cgagggc        57

<210> SEQ ID NO 125
<211> LENGTH: 60
<212> TYPE: DNA
<213> ORGANISM: Leishmania infantum

<400> SEQUENCE: 125
caattacata tgcagcggct ggtgctccaa ttaggatccc tacgacgtcc gcggcagcgc     60

<210> SEQ ID NO 126
<211> LENGTH: 69
<212> TYPE: DNA
<213> ORGANISM: Leishmania infantum

<400> SEQUENCE: 126
caattacata tgtgcattgc tcttggcatc gtccaattaa agcttctggg gcgtgaagcg     60
tatgtactc                                                            69
```

COMPOUNDS AND METHODS FOR DIAGNOSIS AND TREATMENT OF LEISHMANIASIS

PRIORITY CLAIM

This application claims priority to U.S. Provisional Application 60/791,226 filed Apr. 10, 2006. The foregoing application is hereby incorporated by reference in its entirety as if fully set forth herein.

This application claims priority to U.S. Provisional Application 60/744,798 filed Apr. 13, 2006. The foregoing application is hereby incorporated by reference in its entirety as if fully set forth herein.

STATEMENT REGARDING FEDERALLY SPONSORED RESEARCH OR DEVELOPMENT

This invention was made in part with government support under Grant No. AI-25038 awarded by the National Institutes of Health. The government has certain rights in this invention.

FIELD OF THE INVENTION

The present invention relates generally to the serodiagnosis of *Leishmania* infection. The invention is more particularly directed to the use of one or more *Leishmania* polypeptides in methods and diagnostic kits to screen organisms and blood supplies for *Leishmania*, and to identify those individuals that are likely to progress to acute visceral leishmaniasis. The invention is also directed to vaccines and pharmaceutical compositions for treating and immunizing an organism against leishmaniasis.

BACKGROUND OF THE INVENTION

*Leishmania* organisms are intracellular protozoan parasites of macrophages that cause a wide range of clinical diseases in humans and domestic animals, primarily dogs. In some infections, the parasite may lie dormant for many years. In other cases, the host may develop one of a variety of forms of leishmaniasis. For example, the disease may be asymptomatic or may be manifested as sub-clinical visceral leishmaniasis, which is characterized by mild symptoms of malaise, diarrhea and intermittent hepatomegaly. Patients with sub-clinical or asymptomatic disease usually have low antibody titers, making the disease difficult to detect with standard techniques. Alternatively, leishmaniasis may be manifested as a cutaneous disease, which is a severe medical problem but is generally self-limiting, or as a highly destructive mucosal disease, which is not self-limiting. Finally, and most seriously, the disease may be manifested as an acute visceral infection involving the spleen, liver and lymph nodes, which, untreated, is generally a fatal disease. Symptoms of acute visceral leishmaniasis include hepatosplenomegaly, fever, leukopenia, anemia and hypergammaglobulinemia.

Leishmaniasis is a serious problem in much of the world, including Brazil, China, East Africa, India and areas of the Middle East. The disease is also endemic in the Mediterranean region, including southern France, Italy, Greece, Spain, Portugal and North Africa. The number of cases of leishmaniasis has increased dramatically in the last 20 years, and millions of cases of this disease now exist worldwide. About 2 million new cases are diagnosed each year, 25% of which are visceral leishmaniasis. There are, however, no vaccines or effective treatments currently available.

Diagnosis of Visceral leishmaniasis can not always be made only on the basis of clinical symptoms because visceral leishmaniasis shares its clinical features with other diseases such as malaria, typhoid fever and tuberculosis occurring commonly in the same endemic areas. Thus, the diagnosis of visceral leishmaniasis largely relies on parasitological or serological methods. The former is microscopic detection of amastigotes in aspirates of spleen and bone marrow or detection of promastigotes through cultivation of the aspirates. Unfortunately, this method requires the biopsy of bone marrow, liver, spleen, or lymph nodes may be required, which may lead to secondary infection or further disfigurement of the patient. Additionally, along with being an invasive diagnosis, it takes a long period of time to diagnose and results are commonly non-conclusive. Therefore, this method is invasive, time-consuming, and not sufficiently sensitive, thereby rendering it inefficient.

Less invasive and time consuming laboratory procedures do exist, however, these procedures suffer from either lack of sensitivity or cumbersome implementation. For example the Liquid Direct Agglutination Test (LQ DAT: Ahfad University, Khartoum and IPB, Addis Abbeba) and the Freeze Dried DAT (FD DAT: Meredith et al. 1995) have good sensitivity, but require multiple pipetting steps and incubation, which makes implementation of this test difficult in developing countries. Similarly, the Latex Antigen Agglutination Test in Urine (KATEX®: Kalon Biological Ltd-UK) has good sensitivity and specificity, but requires a cumbersome urine boiling step and further suffers from low reproducibility. Finally, the rK39 and rK26 dipstick tests (Inbios®, Seattle, Wash.) can rapidly give results within a matter of minutes, but these tests lack sensitivity in certain geographic regions such as Sudan, Ethiopia and Kenya. Because the dipstick tests can be easily, quickly, and affordably implemented, yet suffer from lack of antigen sensitivity, discovery of new antigens is necessary for more accurate diagnosis of leishmaniasis.

Among defined leishmanial antigens reported previously, rK39 appears to be the best antigen for serodiagnosis of visceral leishmaniasis in terms of both sensitivity and specificity. rK39 is sensitive and reliable even on a strip format, which is feasible for field use, and the rK39 strip test has high sensitivity in India, Nepal and Brazil. In Sudan, Ethiopia and Kenya, however, the sensitivity of the strip test falls to 67% and the negative responses on the strip test appear to correlate with lower reactivity by ELISA. Thus, new diagnostic antigens are needed to complement rK39 to contribute to the development of a more accurate diagnosis of leishmaniasis. The present invention fulfills these needs and many other related needs.

SUMMARY OF THE INVENTION

Briefly stated, this invention relates to compounds and methods for detecting and treating leishmaniasis in individuals and in blood supplies.

More specifically, compounds and methods are provided for diagnosing, preventing, treating and detecting leishmaniasis infection and stimulating immune responses in patients are disclosed. The compounds disclosed include polypeptides and fusion proteins that contain at least one immunogenic portion of one or more *Leishmania* antigens, or a variant thereof. Additionally, methods of screening a screening library for tandem repeat proteins that have immunogenic properties are disclosed. Vaccines and pharmaceutical compositions comprising polynucleotides, polypeptides, fusion proteins and variants thereof that may be used for the prevention and therapy of leishmaniasis, as well as for the detection of Leishmaniasis infection are described.

In one embodiment a method for detecting *Leishmania* infection is disclosed that comprises the steps of first contacting a biological sample with polypeptides comprising at least one tandem repeat unit, wherein the tandem repeat unit comprises an amino acid sequence having homology to, an amino acid sequence selected from the group consisting of SEQ ID NO: 1-59; and second detecting the presence of antibodies in the biological sample to detect Leishmaniasis infection. Related embodiments include similar methods of using tandem repeat proteins and fusion proteins that comprise one or more of the amino acid sequences of SEQ ID NO: 1-59. In still further embodiments, diagnostic kits for detecting *Leishmania* infection are disclosed that comprise the polypeptides described above.

In still further embodiments of the present invention, DNA sequences encoding the polypeptides described above are disclosed in addition to expression vectors and host cells comprising the same.

Additional embodiments are disclosed wherein the polypeptides disclosed are used in pharmacological compositions and related methods of using these pharmacological compositions to treat, detect, and immunizing against *Leishmania* infection are disclosed.

In other embodiments, methods for screening for immunogenic polypeptides are disclosed, which comprise the steps of constructing a screening library, screening the library with a biological sample and analyzing identified sequences to select for tandem repeat genes. Still further methods are disclosed for embodiments of the present invention where one or more polypeptide or polynucleotide sequences are selected and then screened for tandem repeat domains so as to screen for immunogenic polynucleotides or immunogenic polypeptides.

BRIEF DESCRIPTION OF THE DRAWINGS

Preferred and alternate embodiments of the present invention are described in detail below with reference to the following drawings.

DETAILED DESCRIPTION

Figure 1:
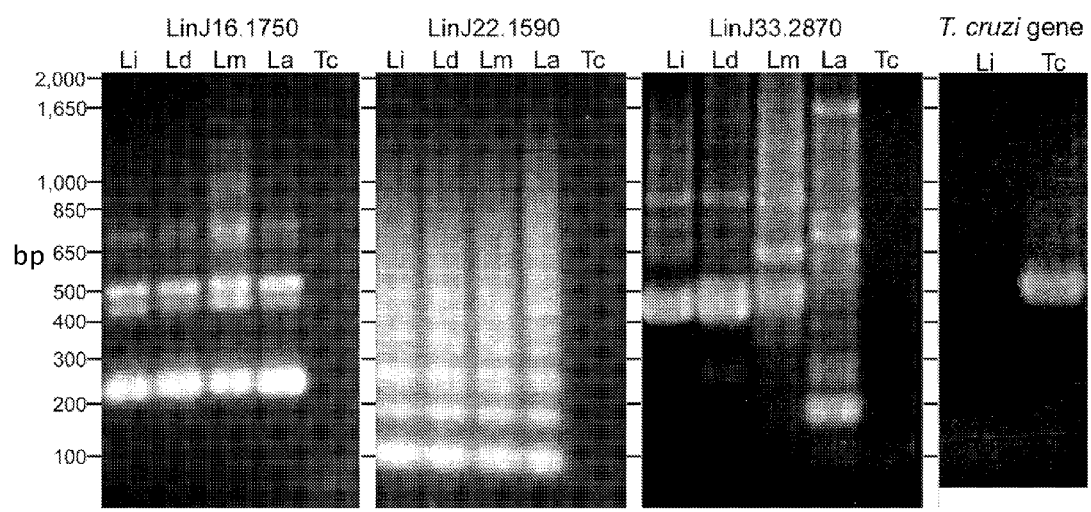
FIG. 1 shows a representative PCR analysis of tandem repeat genes. PCR reactions performed with primer sets specific for the tandem repeat regions of LinJ16.1750, LinJ22.1590 and LinJ33.2870 or for a *T. cruzi* gene using total DNA of *L. infantum* (Li), *L. donovani* (Ld), *L. major* (Lm), *L. amazonensis* (La) and *T. cruzi* (Tc) as templates. Sizes are shown in base pairs.

As stated above the present invention relates to compositions and methods for detecting and protecting against *Leishmania* infection in a biological sample or organism, in addition to methods for screening and identifying compounds that have efficacy in detecting and protecting against *Leishmania* infection in a biological sample or organism.

In one embodiment, the invention provides a method compounds for detecting *Leishmania* infection in a biological sample or organism, comprising: (a) contacting a biological sample with one or more polypeptides at least one of which comprises one or more tandem repeat units or a variant thereof that only differs in conservative substitutions or modifications, which tandem repeat unit in certain embodiments comprises an amino acid sequence having at least 8 consecutive amino acids of, and at least 70% sequence homology to, an amino acid sequence selected from SEQ ID NOS:1-59, under conditions and for a time sufficient for binding to the polypeptide(s) by an antibody in the sample to take place; and (b) detecting in the biological sample the presence of one or a plurality of antibodies that specifically bind to the polypeptide, thereby detecting *Leishmania* infection in the biological sample.

In another embodiment, the invention provides methods and compositions for detecting *Leishmania* infection in a biological sample or organism, comprising: (a) contacting a biological sample with a composition comprising a polypeptide that comprises a tandem repeat unit, or a variant thereof that only differs in conservative substitutions or modifications under conditions and for a time sufficient for binding to the polypeptide(s) by an antibody in the sample to take place; and (b) detecting in the biological sample the presence of antibodies that bind to the polypeptide, thereby detecting *Leishmania* infection in the biological sample. In these and other related embodiments the composition may include a single tandem repeat as provided herein, or may include two or more tandem repeat units which may be the same or different. This composition may thus comprise one or more species of tandem repeat unit, and/or may also include fusion proteins comprising one or more species of tandem repeat unit.

In a still further embodiment, the invention provides methods for screening and selecting tandem repeat proteins that have efficacy in detecting *Leishmania* infection in a biological sample or organism comprising: (a) constructing a *Leishmania* screening library; (b) screening the *Leishmania* screening library; and (c) analyzing the genes identified from the screening the *Leishmania* screening library to select genes that are tandem repeat genes.

In yet another embodiment, the invention provides systems and methods for treating and detecting leishmaniasis in patients with clinical or sub-clinical leishmaniasis infection.

Polypeptides that are contemplated according to certain embodiments of the present invention include, but are not limited to, polypeptides comprising immunogenic portions of *Leishmania* antigens comprising the sequences recited in SEQ ID NO:1-59. As used herein, the term "polypeptide" encompasses amino acid chains of any length, including full length proteins (i.e., antigens), wherein the amino acid residues are covalently linked as linear polymers by peptide bonds. Thus, a polypeptide comprising an immunogenic portion of one of the above antigens may consist entirely of the immunogenic portion, or may contain additional sequences. The additional sequences may be naturally occurring sequences such as sequences derived from the native *Leishmania* antigen, or may be heterologous (e.g., derived from other sources including exogenous naturally occurring sequences and/or artificial sequences), and such sequences may (but need not) be immunogenic. An antigen "having" a particular recited sequence is an antigen that comprises a recited sequence, e.g., that contains, within its full length sequence, the recited sequence. The native antigen may, or may not, contain one or more additional amino acid sequences. A material, molecule, preparation or the like which is "isolated" refers to its having been removed from the environment or source in which it naturally occurs. For example, a polynucleotide sequence which is part of a gene present on a chromosome in a subject or biological source such as an intact, living animal is not isolated, while DNA extracted from a biological sample that has been obtained from such a subject or biological source would be considered isolated. In like fashion, "isolating" may refer to steps taken in the processes or methods for removing such a material from the natural environment in which it occurs.

As used herein, the term "tandem repeat" refers to a region of a polynucleotide sequence (e.g., a sequence of DNA, RNA, recombinantly engineered or synthetic oligonucleotides including linear polymers of non-naturally occurring nucleotides or nucleotide analogs or the like, including nucleotide mimetics) or to a region of a polypeptide or protein comprising a sequence, respectively, of about 6 to 1200 nucleotides or 2 to 400 amino acids, that is repeated in tandem such that the sequence occurs at least two times. As used herein the term "tandem repeat unit" refers to a single unit of the sequence that is repeated in tandem. Additionally, the term "tandem repeat" also encompasses a region of DNA wherein more than a single 2- to 400-amino acid or 6- to 1200-nucleotide tandem repeat unit is repeated in tandem or with intervening bases or amino acids, provided that at least one of the sequences is repeated at least two times in tandem. Moreover, the term "tandem repeat" also encompasses regions of DNA or a protein wherein the tandem repeat units are not identical. Where two or more sequences are at least 70% homologous to each other or are reasonable variants of each other, these sequences will be considered tandem repeat units for the purpose of comprising and constituting a tandem repeat.

Also, where a sequence is at least 6, 7, 8, 9, 10, 11, 12, 13, 14, 15, 16, 17, 18, 19, 20, 21, 22 or more amino acids of a tandem repeat unit, this sequence will be considered a tandem repeat unit for the purpose of comprising and constituting a tandem repeat.

Also, where a sequence is at least about 18, 21, 24, 27, 30, 33, 36, 39, 42, 45, 48, 51 or any intervening integer of nucleotides, the sequence will be considered a tandem repeat unit for the purpose of comprising and constituting a tandem repeat.

Additionally, the term "tandem repeat" also encompasses tandem repeats where one or more tandem repeat unit of a tandem repeat is the reverse sequence of the other tandem repeat units. Reverse tandem repeat units and non-reverse tandem repeats can be configured in any way and with or without intervening nucleotide bases or amino acids. Configurations of reverse and non-reverse sequences include, but are not limited to, those where a non-reverse sequence is followed by reverse sequence; where a reverse sequence is followed by non-reverse sequence; and where a reverse sequence is followed by a reverse sequence. In the case of double-stranded polynucleotides having tandem repeats two or more such repeats may be present on the same strand or may occur on opposite strands.

In certain preferred embodiments a tandem repeat may comprise an immunogenic portion of a *Leishmania* antigen. An immunogenic portion of a *Leishmania* antigen is a portion that is capable of eliciting an immune response (i.e., cellular and/or humoral) in a presently or previously *Leishmania*-infected patient (such as a human or a dog) and/or in cultures of lymph node cells or peripheral blood mononuclear cells (PBMC) isolated from presently or previously *Leishmania*-infected individuals. Those skilled in the art will be familiar with any of a wide variety of methodologies and criteria for determining whether an immune response has been elicited. (See, e.g., Current Protocols in Immunology, John Wiley & Sons Publishers, NY 2000, Chapter 2, Units 2.1-2.3) The cells in which a response is elicited may comprise a mixture of cell types or may contain isolated component cells (including, but not limited to, T-cells, NK cells, macrophages, monocytes and/or B cells). In particular, immunogenic portions are capable of inducing T-cell proliferation and/or a dominantly Th1-type cytokine response (e.g., IL-2, IFN-.gamma., and/or TNF-.alpha. production by T-cells and/or NK cells; and/or IL-12 production by monocytes, macrophages and/or B cells). Immunogenic portions of the antigens described herein may generally be identified using techniques known to those of ordinary skill in the art, including the representative methods provided herein.

The compositions and methods of the present invention also encompass variants of the above polypeptides. A polypeptide "variant," or a polypeptide that is "homologous" to another protein as used herein, is a polypeptide that differs from a native (e.g., naturally occurring) protein in one or more substitutions, deletions, additions and/or insertions, such that the immunogenicity of the polypeptide is not substantially diminished. For instance, the ability of a variant to react with an antigen-specific antibody, antiserum or T cell may be enhanced or unchanged, relative to the native protein, or may be diminished by less than 50%, and preferably less than 20%, relative to the native protein. Such variants may generally be identified by modifying one of the herein described polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1-30 amino acids, preferably 5-15 amino acids) has been removed from the N- and/or C-terminal of the mature protein.

Polypeptide variants encompassed by the present invention include those exhibiting at least about 70%, 75%, 80%, 85%, 90%, 91%, 92%, 93%, 94%, 95%, 96%, 97%, 98%, 99% or more identity (determined as described below) to the polypeptides disclosed herein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

The polypeptides of the present invention can be prepared in any suitable manner known in the art. Such polypeptides include naturally occurring polypeptides, recombinantly produced polypeptides, synthetically produced polypeptides, or polypeptides produced by a combination of these methods. Similarly certain embodiments disclosed herein contemplate polynucleotides comprised of the naturally occurring polynucleotides having sugar—(e.g., ribose or deoxyribose) phosphate backbones in 5'-to-3' linkage, but the invention is not so limited and also contemplates polynucleotides comprised of any of a number of natural and/or artificial polynucleotide analogs and/or mimetics, for example those designed to resist degradation or having other desirably physicochemical properties such as synthetic polynucleotides having a phosphorothioate backbone, or the like.

Polynucleotides may comprise a native sequence (i.e., an endogenous sequence that encodes a protein or a portion thereof) or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not diminished, relative to a native tumor protein. The effect on the immunogenicity of the encoded polypeptide may generally be assessed as described herein. The term "variants" also encompasses homologous genes of xenogenic origin.

When comparing polynucleotide or polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci. USA 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Therefore, the present invention encompasses polynucleotide and polypeptide sequences having substantial identity to the sequences disclosed herein, for example those comprising at least 50% sequence identity, preferably at least 55%, 60%, 65%, 70%, 75%, 80%, 85%, 90%, 95%, 96%, 97%, 98%, or 99% or higher, sequence identity compared to a polynucleotide or polypeptide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

In additional embodiments, the present invention provides isolated polynucleotides and polypeptides comprising various lengths of contiguous stretches of sequence identical to or complementary to one or more of the sequences disclosed herein. For example, polynucleotides are provided by this invention that comprise at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative DNA segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

In other embodiments, the present invention is directed to polynucleotides that are capable of hybridizing under moderately stringent conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5.times. SSC, 0.5% SDS, 1.0 mM EDTA (pH 8.0); hybridizing at 50.degree. C.-65.degree. C., 5×SSC, overnight; followed by washing twice at 65.degree. C. for 20 minutes with each of 2.times., 0.5.times. and 0.2.times. SSC containing 0.1% SDS.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

"Polypeptides" as described herein also include combination polypeptides, also referred to as fusion proteins. A "combination polypeptide" or "fusion protein" is a polypeptide comprising at least one of the above immunogenic portions and one or more additional immunogenic *Leishmania* sequences, which are joined via a peptide linkage into a single amino acid chain. The sequences may be joined directly (i.e., with no intervening amino acids) or may be joined by way of a linker sequence (e.g., Gly-Cys-Gly) that does not significantly diminish the immunogenic properties of the component polypeptides.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in frame. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

In on embodiment of the present invention fusion proteins comprise one or more tandem repeat units. In further embodiments the one or more tandem repeat units are selected from a group consisting of SEQ ID NO. 1-59. In still further embodiments, fusion proteins further comprise the antigenic portions of proteins such as, but not limited to, rK26, rK39 and rLiA2, which are specifically disclosed in SEQ ID NO.'s 119-121.

Methods of Screening for Immunogenic Polypeptides

In one embodiment, the invention provides methods for screening and selecting tandem repeat proteins that may be useful in diagnosis, treatment and/or immunization of a subject or biological source such as a human patient, for example, in detecting *Leishmania* infection in a biological sample or in an organism, comprising: (a) constructing a *Leishmania* screening library; (b) screening the *Leishmania* screening library; and (c) analyzing the genes identified from the screening the *Leishmania* screening library to select genes that are tandem repeat genes. In further embodiments, a screening library can be constructed from the genomic DNA of any organism, for example by way of illustration and not limitation, an infectious or non-infectious organism, or an infectious organism that may be pathogenic or non-pathogenic, such as a bacterium, a virus, a protozoan, a fungus, a yeast, a diplomonoadid and a kinetoplastid. In certain embodiments the screening library may be constructed from genetic material (i.e., nucleic acid) or an organism that causes or is capable of causing leishmaniasis, such as *Leishmania infantum, Leishmania donovani, Leishmania major, Leishmania amazonensis, Trypanosoma cruzi*, or a natural or unnatural bacterial strain that causes leishmaniasis In a still further embodiment, libraries can be constructed with nucleotide species, including but not limited to DNA and cDNA.

For instance, one such embodiment contemplates a method of identifying an immunogenic polypeptide for diagnosis, treatment or immunization in a patient, comprising (a) expressing, in one or a plurality of host cells, expression products of a polynucleotide expression library which comprises one or a plurality of candidate immunogenic polypeptide-encoding polynucleotides at least one of which is capable of expressing a candidate immunogenic polypeptide that comprises a tandem repeat, to obtain a host cell population comprising expression products (b) contacting, under conditions and for a time sufficient for specific binding of at least one antibody in the biological material to at least one expression product, (i) the host cell population comprising expression products of (a) with (ii) a biological material that is obtained from a subject or biological source that has been infected with an infectious or non-infectious organism, or with a pathogenic or non-pathogenic infectious organism such as a bacterium, a virus, a protozoan, a fungus, a yeast, a diplomonoadid or a kinetoplastid, or with a *Leishmania* organism or other organism that is capable of causing leishmaniasis, wherein the biological material comprises at least one antibody and is selected from blood, serum and urine (c) detecting at least one host cell that comprises the at least one expression product to which the at least one antibody specifically binds; (d) isolating from the host cell detected in (c) a polynucleotide that encodes the expression product to which the at least one antibody specifically binds to obtain an isolated polynucleotide; and (e) analyzing a nucleotide sequence of the isolated polynucleotide of (d) for presence or absence of a tandem repeat, wherein the presence of a tandem repeat indicates the isolated polynucleotide encodes an immunogenic polypeptide, and therefrom identifying the immunogenic polypeptide.

Constructing a polynucleotide screening library such as a polynucleotide expression library as described herein can be achieved by cleaving or shearing DNA with methods such as sonication or enzyme restriction, which are well known in the art. Resulting nucleotide fragments can be of any size, however, preferably averaging 1, 2, or 3 kb. Resulting nucleotide fragments are then amplified through methods that are well known in the art such as ligation into recombinant polynucleotide vectors including amplification and/or expression vectors and expression with expression vectors such as the λ phage vector or the ZAP Express© vector (Stratagene, La Jolla, Calif.), to generate a polynucleotide screening library, for instance, a polynucleotide expression library. The screening library is then screened by exposing biological material to host cells comprising the expressed expression library products where the biological material may be sera, blood, urine, saliva, or any biological material that has been obtained from a subject or biological source that has been, or is, infected by *Leishmania infantum, Leishmania donovani, Leishmania major, Leishmania amazonensis, Trypanosoma cruzi*, or other natural or unnatural strains of bacteria that causes leishmaniasis. The host cell can be a higher eukaryotic cell, such as a mammalian cell (including a tumor cell), or a lower eukaryotic cell, such as a yeast cell, or the host cell can be a prokaryotic cell, such as a bacterial cell. Representative examples of appropriate host cells according to the present invention include, but need not be limited to, bacterial cells, such as *E. coli, Streptomyces, Salmonella typhimurium*; fungal cells, such as yeast; insect cells, such as *Drosophila* S2 and *Spodoptera* Sf9; animal cells, such as CHO, COS or 293 cells; adenoviruses; plant cells, or any suitable cell already adapted to in vitro propagation or so established de novo. The selection of an appropriate host is deemed to be within the scope of those skilled in the art from the teachings herein. Various mammalian cell culture systems can also be employed to express recombinant protein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa, and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, for example, calcium phosphate transfection, DEAE-Dextran mediated transfection, electroporation (e.g., Davis et al., 1986 Basic Methods in Molecular Biology) or other techniques known to the art.

Host cells expressing expression products that comprise an immunogenic polypeptide (e.g., a polypeptide that reacts with an antibody present in a test biological material via a specific binding interaction) may be identified according to any of a number of known methodologies. Readily observed host cell expression of an expression library product, for example, resulting plaques within the expression library, can then be detected, and the original antigenic epitope-encoding polynucleotide fragments may be excised from the expression vector and recovered. In alternative embodiments, the screening library is derived from a subject or biological source that has been exposed to biological material infected by an organism (e.g., an infectious organism) such as a pathogenic or non-pathogenic bacteria, protozoan, fungus, yeast, virus, a diplomonadid, a kinetoplastid or other infectious organism. The excised nucleotide fragments can then be sequenced using methods that are well known in the art. In an additional embodiment these sequences are compared to known genes, which can be found in databases such as the *Leishmania infantum* data gene database (GeneDB: The Wellcome Trust Sanger Institute, www.genedb.org), or the GenBank gene database (National Center for Biotechnology Information (NCBI) www.ncbi.nih.gov).

The nucleotide sequences obtained from sequencing the nucleotide fragments are then analyzed to determine if these sequences comprise tandem repeats. Tandem repeats can be identified, for example, using Tandem Repeats Finder (http://tandem.bu.edu/trf/trf.htm) or other similar programs or methods that identify tandem repeats. Typically, these programs or methods identify the period size of the tandem repeats and the number of copies aligned with the consensus pattern. In one embodiment of the present invention, screening may exclude small tandem repeat motifs that have a period size (e.g., periodicity) of about 24, 21, 18, 15, 12 or 10 base pairs or less.

In yet another embodiment, sequence libraries or genomes of any organism can be screened for tandem repeats to find epitopes that can be used for the serodiagnosis or treatment of diseases including, but not limited to leishmaniasis, tuberculosis, HIV, and cancer. Where one or more sequences of DNA, cDNA, RNA, or amino acids of any organism are known, these sequences can be screened for tandem repeats. As described above, programs such a Tandem Repeats Finder can be used to analyze and identify sequences that comprise tandem repeats, which are likely to comprise epitopes that are useful in the serodiagnois or treatment of a disease. In one embodiment, the genome of *L. infantum* is screened for tandem repeats.

In a further embodiment, tandem repeat sequences that are identified from a sequence library are subsequently screened by exposure to a biological sample from an infected individual or blood supply to identify tandem repeat sequences that have the greatest efficacy in the serodiagnosis or treatment of a disease.

In a still further embodiment, the tandem repeat unit or units from the identified sequences are isolated and used to construct new proteins with one or more tandem repeat units of one or more sequence of tandem repeat unit. For example, among other possibilities, constructed proteins can comprise a single tandem repeat unit, multiple tandem repeat units, or be a fusion protein with one or more tandem repeat units, with the tandem repeat units being of different or homologous sequences.

Examples of tandem repeat units discovered through these and other methods are disclosed in SEQ ID NO's 1-59.

In a yet further embodiment of the present invention, the tandem repeat units or tandem repeat sequences identified by the aforementioned methods are subsequently screened for homology to other known or unknown proteins. As used herein the term "least homology" refers to a subset of one or more sequences that have less homology to one or more reference sequence compared to at least one sequence within the set. Reference sequences may be, for example, the sequences of polypeptides of organisms that potentially infect organisms that are potentially infected by leishmaniasis, or organisms that are potentially infected by leishmaniasis. Homology screening can be achieved by the methods of homology screening described above, or by the many methods that are well known in the art. For example, tandem repeat sequences or tandem repeat units can be screened for homology to known parasites such as *Trpanosoma Cruzi*, which are potentially present in patients who are being tested for Leishmaniasis. By screening for proteins that are not homologous to proteins in such parasites, proteins can be selected for pharmaceutical or diagnostic purposes that will have more specificity to the disease being treated or tested for, which in this example is Leishmaniasis. By screening for proteins with high specificity to Leishmaniasis, false positives and misdiagnosis can be avoided.

In a still further embodiment, the tandem repeat units or tandem repeat sequences identified by the aforementioned methods are subsequently screened for homology to other known or unknown proteins in mammals such as mouse, dog or human, which are potential hosts or test hosts for Leishmaniasis. Screening for low homology to proteins in these mammals again allows pharmaceutical and diagnostic applications to have more specificity to Leishmaniasis and reduces or eliminates false positives or misdiagnosis.

In yet further embodiments, the screening methods described above can be applied to any disease.

Compounds and Methods for Detecting *Leishmania* Infection

As described above, the present invention discloses methods of screening and selecting tandem repeat proteins that have efficacy in detecting *Leishmania* infection in a biological sample or organism comprising the steps: (a) constructing a *Leishmania* screening library; (b) screening the *Leishmania* screening library; and (c) analyzing the genes identified from the screening the *Leishmania* screening library to select genes that are tandem repeat genes. Polypeptides screened and selected by this and other methods of the present invention can be used for various applications, including but not limited to systems and methods for detecting, treating, preventing, monitoring and immunizing against leishmaniasis infection in organisms or blood supplies.

Accordingly, in another embodiment of this invention, methods are disclosed for detecting and monitoring *Leishmania* infection, in individuals and blood supplies. In general, *Leishmania* infection may be detected in any biological sample that contains antibodies. Preferably, the sample is blood, serum, plasma, saliva, cerebrospinal fluid or urine. More preferably, the sample is a blood or serum sample obtained from a patient or a blood supply. Briefly, *Leishmania* infection may be detected using one or more tandem repeat polypeptides, fusion proteins or other polypeptides as discussed above, or variants thereof. The one or more tandem repeat polypeptides, fusion proteins or other polypeptides are then used to determine the presence or absence of antibodies that are capable of specifically binding to the polypeptide or polypeptides in the sample.

Polypeptides within the scope of the present invention include, but are not limited to, polypeptides comprising immunogenic portions of *Leishmania* antigens comprising the sequences recited in SEQ ID NO:1-59. As used herein, the term "tandem repeat" refers to a region of DNA or a protein comprising a sequence of 4 to forty 400 nucleotides or amino acids repeated in tandem at least two times. As used herein the term "tandem repeat unit" refers to a single unit of the sequence that is repeated in tandem.

As used herein, references to "binding" interactions between two molecules, such as between an antibody and its cognate antigen, may include binding that may according to non-limiting theory be the result of one or more of electrostatic interactions, hydrophobic interactions, steric interactions, van der Waals forces, hydrogen bonding or the like, or other types of interactions influencing such binding events, such as binding of an antibody to a polypeptide, binding of a detection reagent to an antibody/peptide complex, or any other binding interaction of molecules, including in preferred embodiments specific binding interactions wherein in "specific" binding the affinity constant, Ka, may typically be less than about 10-9 M, less than about 10-8 M, less than about 10-7 M, less than about 10-6 M, less than about 10-5 M or less than 10-4 M.

There are a variety of assay formats known to those of ordinary skill in the art for using a polypeptide to detect antibodies in a sample. See, e.g., Current Protocols in Immunology (Coligan et al., eds., John Wiley & Sons, publishers), and Harlow and Lane, Antibodies. A Laboratory Manual, Cold Spring Harbor Laboratory, 1988, which are incorporated herein by reference. In a preferred embodiment, the assay involves the use of a polypeptide (e.g., a polypeptide antigen comprising one or more tandem repeat units as described herein) immobilized on a solid support to bind to and remove the antibody from the sample. The bound antibody may then be detected using a detection reagent that specifically binds to the antibody/polypeptide complex, and that comprises a readily detectable moiety such as a detectable reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized polypeptide after incubation of the polypeptide with the sample. The extent to which components of the sample inhibit the binding of the labeled antibody to the polypeptide is indicative of the reactivity of the sample with the immobilized polypeptide.

The solid support may be any material known to those of ordinary skill in the art to which the polypeptide may be attached. For example, the support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptide may be bound to the solid support using a variety of techniques known to those in the art, which are amply described in the patent and scientific literature. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 mu.g, and preferably about 100 ng, is sufficient to bind an adequate amount of antigen. Nitrocellulose will bind approximately 100 .mu.g of protein per cm.sup.3.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to a support having an appropriate polymer coating using benzoquinone or by condensation of an aldehyde group on the support with an amine and an active hydrogen on the polypeptide (see, e.g., Pierce Immunotechnology Catalog and Handbook (1991) at A12-A13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

Once the polypeptide is immobilized on the support, the remaining protein binding sites on the support are typically blocked. Any suitable blocking agent known to those of ordinary skill in the art, such as bovine serum albumin (BSA) or Tween 20™ (Sigma Chemical Co., St. Louis, Mo.) may be employed. The immobilized polypeptide is then incubated with the sample, and antibody (if present in the sample) is allowed to bind to the antigen. The sample may be diluted with a suitable diluent, such as phosphate-buffered saline (PBS) prior to incubation. In general, an appropriate contact time (i.e., incubation time) is that period of time that is sufficient to permit detection of the presence of antibody within a *Leishmania*-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20.TM. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many sources (e.g., Zymed Laboratories, San Francisco, Calif. and Pierce, Rockford, Ill.).

The detection reagent is then incubated with the immobilized antibody polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-Leishmania antibodies in the sample, the signal detected from the reporter group that remains specifically bound to the solid support is generally compared to a signal that corresponds to an appropriate control according to art-accepted methodologies, for example, a predetermined cut-off value. In one preferred embodiment, the cut-off value may be the average mean signal obtained when the immobilized polypeptide is incubated with samples from an uninfected patient. In general, a sample generating a signal that is three standard deviations above the predetermined cut-off value is considered positive (i.e., reactive with the polypeptide). In an alternate preferred embodiment, the cut-off value is determined using a Receiver Operator Curve, according to the method of Sackett et al., Clinical Epidemiology: A Basic Science for Clinical Medicine, p. 106-7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper lefthand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate.

In a related embodiment, the assay is performed in a flow-through or strip test format, wherein the antigen (e.g., one or ore polypeptides, each comprising at least one tandem repeat unit) is immobilized on a solid support, for instance, a membrane such as nitrocellulose. In the flow-through test, the fluid sample is contacted with the solid support under conditions and for a time sufficient to permit antibodies, if present within the sample, to bind specifically to the immobilized polypeptide as the sample passes through the membrane. A detection reagent (e.g., protein A-colloidal gold) that may be present in the solid support, or that may alternatively be applied, then binds to the antibody-polypeptide complex as the solution containing the detection reagent flows through the membrane. Determination of bound detection reagent may then be performed as described above. In certain related embodiments of the strip test format, one end of a solid support membrane to which the polypeptide antigen is bound, is immersed in a solution containing the sample. The sample migrates along the membrane through a region containing detection reagent and to the area of immobilized polypeptide antigen. Concentration of detection reagent at the area of the immobilized polypeptide antigen indicates the presence of Leishmania antibodies in the sample. Typically, the concentration of detection reagent at that site generates a pattern, such as a line or a series of two or more lines, which can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 1 .mu.g, and more preferably from about 50 ng to about 500 ng. Such tests can typically be performed with a very small amount (e.g., one drop) of patient serum or blood.

Of course, numerous other assay protocols exist that are suitable for use with the polypeptides of the present invention, and these will be known to those familiar with the art for detecting the presence of an antibody that is capable of specifically binding to a particular polypeptide antigen. The above descriptions are intended to be exemplary only.

Systems and Methods of Treating, Preventing, and Immunizing Against Leishmaniasis As described above, the present invention discloses methods of screening and selecting tandem repeat proteins that have efficacy in detecting Leishmania infection in a biological sample or organism comprising the steps: (a) constructing a Leishmania screening library; (b) screening the Leishmania screening library; and (c) analyzing the genes identified from the screening the Leishmania screening library to select genes that are tandem repeat genes. As described herein, polypeptides screened and selected by this and other methods of the present invention can be used for various applications, including but not limited to systems and methods for detecting, treating, preventing, monitoring and immunizing against leishmaniasis infection in organisms or blood supplies.

Accordingly, in certain aspects of the present invention, described in detail below, the polypeptides, antigenic epitopes, tandem repeat units, immunogentic sequences, fusion proteins and/or soluble Leishmania antigens of the present invention may be incorporated into pharmaceutical compositions or vaccines. For clarity, the term "polypeptide" will be used when describing specific embodiments of the inventive therapeutic compositions and diagnostic methods; however, it will be clear to one of skill in the art that the antigenic epitopes, polypeptides, tandem repeat units and fusion proteins of the present invention may also be employed in such compositions and methods.

Pharmaceutical compositions comprise one or more polypeptides, each of which may contain one or more of the above sequences (or variants thereof), and a physiologically acceptable carrier. Vaccines, also referred to as immunogenic compositions, comprise one or more of the above polypeptides and an immunostimulant, such as an adjuvant (e.g., LbeIF4A, interleukin-12 or other cytokines) or a liposome (into which the polypeptide is incorporated). Many adjuvants contain a substance designed to protect the antigen from rapid catabolism, such as aluminum hydroxide or mineral oil, and a stimulator of immune responses, such as lipid A, Bordetella pertussis or Mycobacterium tuberculosis derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2,-7,-12, and other like growth factors, may also be used as adjuvants.

Within certain embodiments of the invention, the adjuvant composition is preferably one that induces an immune response predominantly of the Th1 type. By virtue of its ability to induce an exclusive Th1 immune response, the use of LbeIF4A, and variants thereof, as an adjuvant in the vaccines of the present invention is particularly preferred. Certain other preferred adjuvants for eliciting a predominantly Th1-type response include, for example, Imiquimod, Res-Imiquimod, a combination of monophosphoryl lipid A, preferably 3-de-O-acylated monophosphoryl lipid A, together with an aluminum salt. MPL™ adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., Science 273:352, 1996. Another preferred adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other preferred formulations include more than one saponin in the adjuvant combinations of the present invention, for example combinations of at least two of the following group comprising QS21, QS7, Quil A, .beta.-escin, or digitonin.

Alternatively, the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol.sup.R to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL™ adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL™ adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 is disclosed in WO 00/09159. Preferably the formulation additionally comprises an oil in water emulsion and tocopherol.

Additional illustrative adjuvants for use in the compositions of the invention include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), EnhanZyn.TM. (Corixa, Hamilton, Mont.), RC-529 (Corixa, Hamilton, Mont.) and other aminoalkyl glucosaminide 4-phosphates (AGPs), such as those described in U.S. Pat. No. 6,113,918 and pending U.S. patent application Ser. No. 09/074,720, the disclosures of which are incorporated herein by reference in their entireties, and polyoxyethylene ether adjuvants such as those described in WO 99/52549A1.

Other preferred adjuvants include adjuvant molecules of the general formula (I): HO(CH.sub.2CH.sub.20).sub.n-A-R, wherein, n is 1-50, A is a bond or —C(O)—, R is C.sub.1-50 alkyl or Phenyl C.sub.1-50 alkyl. One embodiment of the present invention consists of a vaccine formulation comprising a polyoxyethylene ether of general formula (I), wherein n is between 1 and 50, preferably 4-24, most preferably 9; the R component is C.sub.1-50, preferably C.sub.4-C.sub.20 alkyl and most preferably C.sub.12 alkyl, and A is a bond. The concentration of the polyoxyethylene ethers should be in the range 0.1-20%, preferably from 0.1-10%, and most preferably in the range 0.1-1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index (12.sup.th edition: entry 7717). These adjuvant molecules are described in WO 99/52549. The polyoxyethylene ether according to the general formula (I) above may, if desired, be combined with another adjuvant. For example, a preferred adjuvant combination is preferably with CpG as described in the pending UK patent application GB 9820956.2.

Vaccines may additionally contain a delivery vehicle, such as a biodegradable microsphere (disclosed, for example, in U.S. Pat. Nos. 4,897,268 and 5,075,109). Pharmaceutical compositions and vaccines within the scope of the present invention may also contain other *Leishmania* antigens, either incorporated into a combination polypeptide or present within one or more separate polypeptides.

Alternatively, a pharmaceutical or immunogenic composition may contain an immunostimulant, such as an adjuvant (e.g., LbeIF4A, interleukin-12 or other cytokines, or DNA coding for such enhancers), and a polynucleotide (e.g., DNA) encoding one or more of the polypeptides or fusion proteins described above, such that the polypeptide is generated in situ. In such compositions, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as *Bacillus*-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., Science 259:1745-1749 (1993) and reviewed by Cohen, Science 259:1691-1692 (1993). The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

In one preferred embodiment, compositions of the present invention include multiple polypeptides selected so as to provide enhanced protection against a variety of Leishmania species. Such polypeptides may be selected based on the species of origin of the native antigen or based on a high degree of conservation of amino acid sequence among different species of Leishmania. A combination of individual polypeptides may be particularly effective as a prophylactic and/or therapeutic vaccine because (1) stimulation of proliferation and/or cytokine production by a combination of individual polypeptides may be additive, (2) stimulation of proliferation and/or cytokine production by a combination of individual polypeptides may be synergistic, (3) a combination of individual polypeptides may stimulate cytokine profiles in such a way as to be complementary to each other and/or (4) individual polypeptides may be complementary to one another when certain of them are expressed more abundantly on the individual species or strain of Leishmania responsible for infection. A preferred combination contains polypeptides that comprise immunogenic portions of M15, Ldp23, Lbhsp83, Lt-1 and LbeIF4A. Alternatively, or in addition, the combination may include one or more polypeptides comprising immunogenic portions of other Leishmania antigens disclosed herein, and/or soluble Leishmania antigens.

In another preferred embodiment, compositions of the present invention include single polypeptides selected so as to provide enhanced protection against a variety of Leishmania species. A single individual polypeptide may be particularly effective as a prophylactic and/or therapeutic vaccine for those reasons stated above for combinations of individual polypeptides.

In another embodiment, compositions of the present invention include individual polypeptides and combinations of the above described polypeptides employed with a variety of adjuvants, such as IL-12 (protein or DNA) to confer a protective response against a variety of Leishmania species.

In yet another embodiment, compositions of the present invention include DNA constructs of the various Leishmania species employed alone or in combination with variety of adjuvants, such as IL-12 (protein or DNA) to confer a protective response against a variety of Leishmania species.

The above pharmaceutical compositions and vaccines may be used, for example, to induce protective immunity against Leishmania in a patient, such as a human or a dog, to prevent leishmaniasis. Appropriate doses and methods of administration for this purposes are described in detail below.

The pharmaceutical and immunogenic compositions described herein may also be used to stimulate an immune response, which may be cellular and/or humoral, in a patient. For Leishmania-infected patients, the immune responses that may be generated include a preferential Th1 immune response (i.e., a response characterized by the production of the cytokines interleukin-1, interleukin-2, interleukin-12 and/or interferon-.gamma., as well as tumor necrosis factor-.alpha.). For uninfected patients, the immune response may be the production of interleukin-12 and/or interleukin-2, or the stimulation of gamma delta T-cells. In either category of patient, the response stimulated may include IL-12 production. Such responses may also be elicited in biological samples of PBMC or components thereof derived from Leishmania-infected or uninfected individuals. As noted above, assays for any of the above cytokines may generally be performed using methods known to those of ordinary skill in the art, such as an enzyme-linked immunosorbent assay (ELISA).

Suitable pharmaceutical compositions and vaccines for use in this aspect of the present invention are those that contain at least one polypeptide comprising an immunogenic portion of a Leishmania antigen disclosed herein (or a variant thereof). Preferably, the polypeptides employed in the pharmaceutical compositions and vaccines are complementary, as described above. Soluble Leishmania antigens, with or without additional polypeptides, may also be employed.

The pharmaceutical compositions and vaccines described herein may also be used to treat a patient afflicted with a disease responsive to IL-12 stimulation. The patient may be any warm-blooded animal, such as a human or a dog. Such diseases include infections (which may be, for example, bacterial, viral or protozoan) or diseases such as cancer. In one embodiment, the disease is leishmaniasis, and the patient may display clinical symptoms or may be asymptomatic. In general, the responsiveness of a particular disease to IL-12 stimulation may be determined by evaluating the effect of treatment with a pharmaceutical composition or vaccine of the present invention on clinical correlates of immunity. For example, if treatment results in a heightened Th1 response or the conversion of a Th2 to a Th1 profile, with accompanying clinical improvement in the treated patient, the disease is responsive to IL-12 stimulation. Polypeptide administration may be as described below, or may extend for a longer period of time, depending on the indication. Preferably, the polypeptides employed in the pharmaceutical compositions and vaccines are complementary, as described above. A particularly preferred combination contains polypeptides that comprise immunogenic portions of LmSTI1, Ldp23, Lbhsp83, Lt-1 and LbeIF4A, Lmsp1a, Lmsp9a, and TSA. Soluble Leishmania antigens, with or without additional polypeptides, may also be employed.

Routes and frequency of administration, as well as dosage, for the above aspects of the present invention will vary from individual to individual and may parallel those currently being used in immunization against other infections, including protozoan, viral and bacterial infections. In general, the pharmaceutical compositions and vaccines may be administered by injection (e.g., intracutaneous, intramuscular, intravenous or subcutaneous), intranasally (e.g., by aspiration) or orally. Between 1 and 12 doses may be administered over a 1 year period. For therapeutic vaccination (i.e., treatment of an infected individual), 12 doses are preferably administered, at one month intervals. For prophylactic use, 3 doses are preferably administered, at 3 month intervals. In either case, booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from leishmaniasis for at least 1-2 years. In general, the amount of polypeptide present in a dose (or produced in situ by the DNA in a dose) ranges from about 100 ng to about 1 mg per kg of host, typically from about 10 .mu.g to about 100 .mu.g. Suitable dose sizes will vary with the size of the patient, but will typically range from about 0.1 mL to about 5 mL.

In another aspect, this invention provides methods for using one or more of the polypeptides described above to diagnose Leishmania infection in a patient using a skin test. As used herein, a "skin test" is any assay performed directly on a patient in which a delayed-type hypersensitivity (DTH) reaction (such as induration and accompanying redness) is measured following intradermal injection of one or more polypeptides as described above. Such injection may be achieved using any suitable device sufficient to contact the polypeptide or polypeptides with dermal cells of the patient, such as a tuberculin syringe or 1 mL syringe. Preferably, the reaction is measured at least 48 hours after injection, more preferably 72 hours after injection.

The DTH reaction is a cell-mediated immune response, which is greater in patients that have been exposed previously to a test antigen (i.e., an immunogenic portion of a polypeptide employed, or a variant thereof). The response may be measured visually, using a ruler. In general, induration that is greater than about 0.5 cm in diameter, preferably greater than about 1.0 cm in diameter, is a positive response, indicative of Leishmania infection, which may or may not be manifested as an active disease.

The polypeptides of this invention are preferably formulated, for use in a skin test, as pharmaceutical compositions containing at least one polypeptide and a physiologically acceptable carrier, as described above. Such compositions typically contain one or more of the above polypeptides in an amount ranging from about 1 .mu.g to 100 .mu.g, preferably from about 10 .mu.g to 50 .mu.g in a volume of 0.1 mL. Preferably, the carrier employed in such pharmaceutical compositions is a saline solution with appropriate preservatives, such as phenol and/or Tween .sub.80T.

The inventive polypeptides may also be employed in combination with one or more known Leishmania antigens in the diagnosis of leishmaniasis, using, for example, the skin test described above. Preferably, individual polypeptides are chosen in such a way as to be complementary to each other. Examples of known Leishmania antigens which may be usefully employed in conjunction with the inventive polypeptides include K39 (Burn et al., Proc. Natl. Acad. Sci. USA, 1993 90:775-779).

The following examples are offered by way of illustration, and not by way of limitation.

EXAMPLES

Example 1

Parasite and Infection of Hamsters

Leishmania infantum, Leishmania donovani, Leishmania major, Leishmania amazonensis and Trypanosoma cruzi were used to infect Hamsters and thereby produce infected sera. Hamsters were infected intracardiacally with $1\times10^7$ Leishmania infantum, Leishmania donovani, Leishmania major, Leishmania amazonensis or Trypanosoma cruzi promastigotes in a stationary phase. After eight to twelve weeks the infected hamsters were sacrificed and the sera were collected.

Example 2

Patient Sera

Sudanese visceral leishmaniasis patient sera were collected from patients with active disease diagnosed clinically and proven parasitologically. Patient sera of cutaneous leishmaniasis (Brazil), tuberculosis (USA) and malaria (Brazil) were collected from well-characterized patients, including parasitological diagnosis (cutaneous leishmaniasis, malaria) or culture positive diagnosis (tuberculosis). Normal sera were obtained from healthy individuals in the United States.

Example 3

Serological Screening of L. infantum Expression Library

Construction and screening of library was performed. In brief, total DNA from L. infantum was randomly sheared by sonication to an average size of ~2 kb, blunt ended with T4 DNA polymerase, and followed by the addition of EcoRI adaptors. The insert was subsequently ligated into the ZAP Express© vector predigested with EcoRI (Stratagene, La Jolla, Calif.) and packaged using Gigapack III© Gold Packaging Extract (Stratagene). The phage library was amplified and then screened according to the manufacturer's instruction with pooled L. infantum-infected hamster sera or pooled Sudanese visceral leishmaniasis patient sera described above. Approximately $5\times10^5$ plaques were screened using the sera at a dilution of 1:100 and immunoreactive plaques were detected with the alkaline phosphatase-conjugated goat anti-hamster IgG or goat anti-human IgG (KPL, Gaithersburg, Md.) and the substrate, BCIP/NBT (KPL). PBK-CMV phagemid vectors were excised from the immunoreactive phage clones according to the manufacturer's protocol. The inserts were sequenced and analyzed using Leishmania infantum gene database (GeneDB: The Wellcome Trust Sanger Institute, www.genedb.org).

Example 4

Tandem Repeat Gene Analysis

The genes identified by the screening were analyzed to determine whether they are tandem repeat genes. Tandem Repeats Finder, a program to locate and display tandem repeats in DNA sequences, was used for this analysis tandem-.bu.edu/trf/trf.html). As a control for the screened genes, 108 genes which were randomly picked from the L. infantum gene database were also analyzed for the presence of tandem repeat motifs. The program calculates the score according to the nature of the tandem repeat genes such as the period size of the repeat, the number of copies aligned with the consensus pattern and the percent of matches between adjacent copies overall. In this study the genes were regarded as tandem repeat genes if the scores from the Tandem Repeats Finder analysis were higher than 500, thus excluding genes containing small tandem repeat motifs such as LinJ01.0470 and LinJ13.0810 (Table I).

TABLE I

L. infantum proteins identified by serological screening

| | GENE DB | | TR analysis | | |
|---|---|---|---|---|---|
| ID | Gene | Size | PS | CN | Score |
| LinJ01.0470 | hypothetical protein | 151 | 3 | 11 | 66 |
| LINJ03.0120 | hypothetical protein | 237 | 117 | 31.8 | 7033 |
| LinJ05.0380 | microtubule-associated protein | 165 | 114 | 28.5 | 6336 |
| LinJ05.0590 | hypothetical protein | 86 | | | |
| LinJ08.0860 | mitochondrial DNA polymerase beta-PAK | 154 | | | |
| LinJ08.1010 | stress-induced protein sti1 | 62 | | | |
| LinJ08.1130 | hypothetical protein | 50 | | | |
| LinJ10.1460 | hypothetical protein | 56 | | | |
| LinJ13.0810 | hypothetical protein | 76 | 15 | 3.7 | 74 |
| LinJ14.1160 | kinesin K39 (rK39) | 241 | 117 | 27.9 | 5237 |
| LinJ14.1190 | kinesin K39 | 95 | 105 | 6.2 | 1198 |
| LinJ14.1540 | hypothetical protein | 112 | 72 | 6.1 | 806 |
| LinJ15.0490 | tb-292 membrane associated protein-like | 164 | 105 | 31.6 | 6027 |
| LinJ16.1540 | kinesin | 230 | 42 | 138.5 | 10588 |
| LinJ16.1560 | kinesin | 88 | 42 | 2.5 | 172 |
| LinJ16.1750 | hypothetical protein | 346 | 219 | 8.7 | 3691 |
| LinJ17.0100 | elongation factor 1-alpha | 49 | | | |
| LinJ17.0610 | hypothetical protein | 86 | | | |
| LinJ18.0610 | hypothetical protein | 68 | | | |
| LinJ18.1150 | hypothetical protein | 107 | | | |
| LinJ21.0440 | 1a RNA binding protein | 37 | | | |
| LinJ22.0680 | hypothetical protein | 45 | 30 | 34.2 | 1137 |
| LinJ22.1590 | hypothetical protein | 234 | 84 | 29.2 | 3993 |
| LinJ24.1570 | basal body component | 164 | | | |
| LinJ26.0980 | dynein heavy chain | 458 | | | |
| LinJ26.1200 | Hsp70.4 heat shock protein 70 | 70 | | | |
| LinJ27.0290 | nucleoporin | 159 | 27 | 2.4 | 74 |
| LinJ27.0410 | calpain-like cysteine peptidase | 702 | 12 | 2.6 | 53 |
| LinJ27.1480 | hypothetical protein | 247 | | | |
| LinJ28.2310 | glycoprotein 96-92 | 61 | 315 | 2.2 | 1398 |
| LinJ28.3170 | hypothetical protein | 75 | 60 | 23.4 | 2546 |
| LinJ31.0530 | amastin | 21 | | | |
| LinJ31.1430 | hypothetical protein | 95 | | | |
| LinJ32.2730 | hypothetical protein | 173 | 150 | 10.3 | 2916 |
| LinJ32.2780 | membrane associated protein | 131 | 30 | 60.9 | 3125 |
| LinJ33.2870 | hypothetical protein | 413 | 444 | 7 | 6041 |
| LinJ34.0710 | hypothetical protein | 306 | 168 | 16.3 | 4487 |
| LinJ34.2140 | hypothetical protein | 296 | 249 | 7.4 | 3604 |
| LinJ35.0590 | proteophosphoglycan ppg4 | 536 | 45 | 246.1 | 10667 |
| LinJ35.0600 | proteophosphoglycan ppg3 | — | 135 | 37.8 | 8773 |
| LinJ35.4250 | poly(A) binding protein | 65 | 36 | 3.6 | 111 |
| LinJ36.4560 | chaperonin Hsp60, mitochondrial | 59 | | | |
| LinJ36.4930 | sterol 24-c-methyltransferase | 40 | | | |

ID numbers in GeneDB are temporary and may vary. Sizes are shown in kDa. Data of PS, CN and score in TR analysis are from a program analysis using Tandem Repeats Finder. Tandem repeat genes are shown in bold letters. Blanks in PS, CN and Score columns represent no repeat found in the genes. PS: period size (bp) of the repeat, CN: number of copies aligned with the consensus pattern.

Example 5

PCR Analysis and Cloning of Tandem Repeat Genes

Tandem repeat sequences of LinJ16.1750, LinJ22.1590 or LinJ33.2870 were amplified by PCR using primers corresponding to both ends of a single copy of the tandem repeat (primer sequences are shown in Table II). The entire gene sequence of LinJ28.2310 was amplified by PCR and primers used for this reaction are also shown in Table II. To analyze whether or not those genes are conserved among *Leishmania* species, total DNA of *L. infantum, L. donovani, L. major, L. amazonensis* and *Trypanosoma cruzi* were used as templates. As a control, a *T. cruzi* gene (GenBank: XM_810936) was amplified by PCR using *L. infantum* and *Trypanosoma cruzi* DNA as templates (primer sequence in Table II). For the cloning of the genes for producing recombinant proteins, *L. infantum* total DNA was used as a template for the PCR reactions.

TABLE II

Primers used in this study

| Gene | Primer sequence |
|---|---|
| LinJ16.1750/ SEQ ID NO: 122 | CAA TTA CAT ATG TAC CCG TTC CTA CGG CTG CAA TTA GGA TCC CTA GCG CGA CGC CAG CTC GTC |
| LinJ22.1590/ SEQ ID NO: 123 | CAA TTA CAT ATG GCT GAC CTG AGG GAG CAG CAA TTA GGA TCC CTA CAC CTC GGC GTC CCT GTC |
| LinJ28.2310/ SEQ ID NO: 124 | CAA TTA CAT ATG AGC GCT GCA CCG TCC CAA TTA GAA TTC CTA CGC AAG TCC GAG GGC |

TABLE II-continued

Primers used in this study

| Gene | Primer sequence |
|---|---|
| LinJ33.2870/<br>SEQ ID NO: 125 | CAA TTA CAT ATG CAG CGG CTG GTG CTC<br>CAA TTA GGA TCC CTA CGA CGT CCG CGG<br>CAG CGC |
| T. cruzi<br>XM_810936/<br>SEQ ID NO: 126 | CAA TTA CAT ATG TGC ATT GCT CTT GGC<br>ATCGTC CAA TTA AAG CTT CTG GGG CGT<br>GAA GCG TAT GTA CTC |

Example 6

Expression of Recombinant Proteins

The PCR product corresponding to two copies of LinJ16.1750 repeat (LinJ16.1750r2), three copies of LinJ22.1590 repeat (LinJ22.1590r3), a copy of LinJ33.2870 repeat (LinJ33.2870r1) or an entire gene of LinJ28.2310 was inserted into NdeI/BamHI or NdeI/EcoRI site of pET28 vector. The sequence of the inserts was then analyzed. These pET28 vectors were transformed into E. coli Rosetta for expression of the recombinant proteins. Expression of the recombinant proteins was induced by cultivation with 1M isopropyl-β-D-thiogalactoside. The recombinant proteins were then purified as 6×His-tagged proteins using Ni-NTA agarose (Qiagen Inc., Valencia, Calif.). Purity of the proteins was assessed by Coomassie blue-staining following SDS-PAGE. The concentrations of these proteins were measured by BCA protein assay (Pierce Biotechnology Inc., Rockford, Ill.).

Example 7

Enzyme-Linked Immunosorbent Assay (ELISA)

rLinJ16.1750r2, rLinJ22.1590r3, rLinJ28.2310, rLinJ33.2870, rK39 or L. infantum promastigote soluble lysate antigen (LiSLA) were diluted in ELISA coating buffer, and 96-well plates were coated with rLinJ16.1750r2, rLinJ22.1590r3, rLinJ28.2310, rLinJ33.2870 (200 ng), rK39 (50 ng) or LiSLA (1 µg) followed by blocking with phosphate-buffered saline containing 0.05% Tween-20 and 1% bovine serum albumin. Next, the plates were incubated with patient sera (diluted 1:100) as well as healthy controls and then with horseradish peroxidase-conjugated protein G (Zymed laboratories, South San Francisco, Calif.). The plates were developed with TMB peroxidase substrate (KPL) and read by a microplate reader at a 450 nm wavelength.

Example 8

Detection of Tandem Repeat Genes in Serologically Screened Genes

Pooled sera from L. infantum-infected hamsters or Sudanese visceral leishmaniasis patients were used to screen a L. infantum expression library. A half million plaques covering about eight times L. infantum genomic equivalents were screened. PBK-CMV phagemids were excised from positive clones; the inserts were sequenced and analyzed using GeneDB. A total of 43 genes were identified as genes encoding B-cell antigens (Table I). Some of the genes encoded previously identified antigens such as HSP70 and K39, but most of them encoded previously unidentified antigens.

The genes identified by the screening were then analyzed by Tandem Repeats Finder. In this study, a gene was regarded as a tandem repeat gene if a score from the analysis was 500 or higher thereby excluding genes containing small tandem repeat domains. Of the 43 genes identified by the serological screening, 19 genes were identified as tandem repeat genes (Table I). For example, LinJ16.1750 contained 8.7 copies of a 219 bp sequence and LinJ28.3170 contained 23.4 copies of a 60 bp sequence. With the exception of LinJ14.1160 (known as rK39), these genes were newly identified as genes encoding B-cell antigens. One hundred and eight genes, which were picked randomly from the database (3 genes from each chromosome), were also analyzed with Tandem Repeats Finder to compare the prevalence of tandem repeat genes with that in the genes identified by screening. In contrast to the screened genes, no tandem repeat genes were found in the 108 randomly picked genes.

Example 9

PCR Analysis of Tandem Repeat Genes

PCR amplifications were performed with total DNA from Leishmania species and T. cruzi to analyze whether or not tandem repeat genes were conserved among these parasites. Using sets of primers specific for tandem repeat domains of LinJ16.1750 and LinJ22.1590, the PCR products showed ladder bands corresponding to one or multiple copies of the repeat (FIG. 1). These genes were conserved among Leishmania species because similar band patterns were observed through all four Leishmania species tested. When primers for tandem repeat domains of LinJ33.2870 were used, the PCR product also showed bands which sizes corresponded to one or two copies of the repeat in Leishmania species, but not in L. amazonensis (FIG. 1). When primers for the whole gene of LinJ33.2870 were used, a 1.5 kb band was found in L. infantum and L. donovani, and bands of 2.1 kb and 1.8 kb were found in L. major and L. amazonensis, respectively. In all cases, no bands were found in PCR reactions using T. cruzi DNA. In contrast, a single band with an expected size was found in T. cruzi but not in L. infantum when primers for a T. cruzi gene were used for PCR. Thus, while the tandem repeat genes are not conserved between Leishmania and T. cruzi, they are well conserved between Leishmania spp.

Example 10

Figure 2:
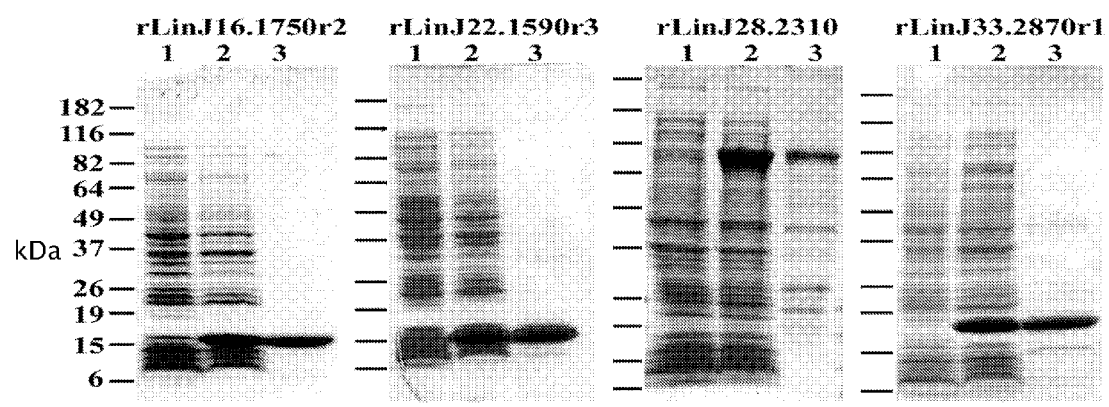
FIG. 2 illustrates an exemplary expression and purification of *L. infantum* recombinant proteins. Shown are coomassie blue-stained SDS/4-20% polyacrylamide gradient gels of uninduced *E. coli* lysates (lane 1), induced lysates (lane 2) and purified proteins (lane 3). Sizes are shown in kDa.

Recognition of Recombinant Tandem Repeat Proteins by Visceral Leishmaniasis Patient Sera To formally test the identified tandem repeat proteins as potential diagnostic candidates, LinJ16.1750r2, LinJ22.1590r3, LinJ28.2310 and LinJ33.2870r1 were expressed as recombinant proteins (FIG. 2).

Figure 3:
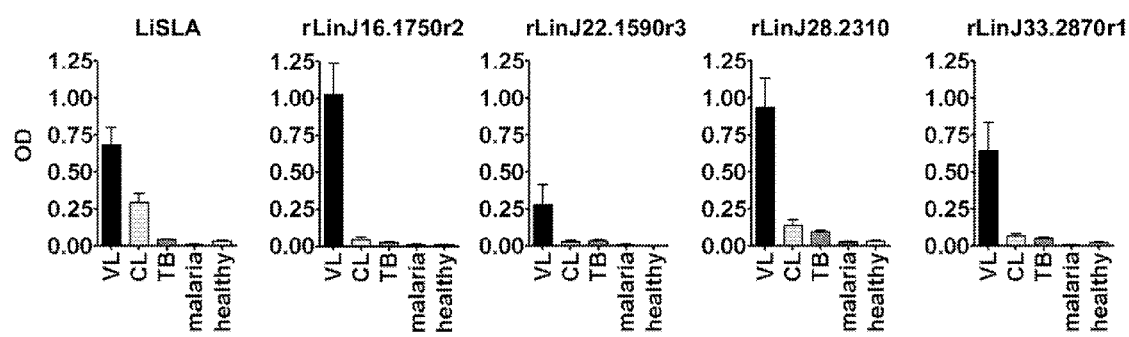
FIG. 3 presents a demonstrative enzyme-linked immunosorbent assay evaluation of patient seroreactivity to *L. infantum* recombinant proteins. Patient sera from patients of visceral leishmaniasis (VL, n=10), cutaneous leishmaniasis (CL, n=10), tuberculosis (TB, n=10), malaria (n=6), or sera from healthy controls in United States (n=10) were used. Mean and SEM of OD values in each group are shown.
Figure 4:
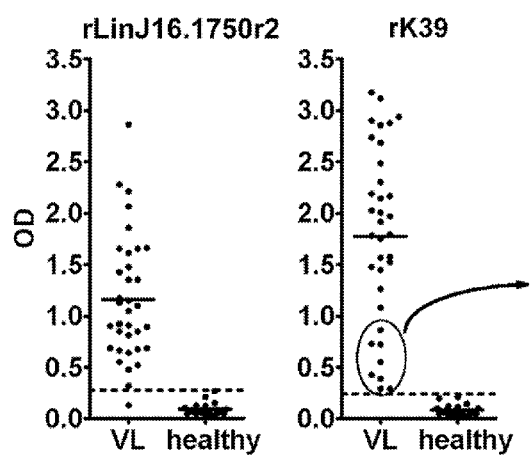
FIG. 4 shows representative reactivity of human visceral leishmaniasis patient sera to tandem repeat proteins. Sera from visceral leishmaniasis patients (n=35) and healthy controls (n=20) were tested for reactivity to rLinJ16.1750r2 or rK39 by ELISA. Mean in each group is shown as a solid line. Dotted lines represent cutoff values calculated as mean+3SD of OD values from healthy controls.

The prevalence of antibodies to the recombinant proteins in a preliminary screen of ten Sudanese visceral leishmaniasis patient sera by ELISA. The visceral leishmaniasis patient sera showed significantly stronger reactivity to all the recombinant proteins than sera from the groups without visceral leishmaniasis, i.e. tuberculosis, malaria and cutaneous leishmaniasis patients or healthy individuals, despite the finding that cutaneous leishmaniasis patients showed antibody responses to LiSLA (FIG. 3). Among the tested proteins, rLinJ16.1750r2 was the best antigen recognized strongly by visceral leishmaniasis patient sera with a high degree of specificity. Next, rLinJ16.1750r2 was tested with additional Sudanese visceral leishmaniasis patient sera. Among 35 sera tested, 34 showed antibody responses to rLinJ16.1750r2 (the cutoff value was the mean+3 SD of healthy controls: FIG. 4). The sensitivity using rLinJ16.1750r2 was 97%, comparable to that of rK39 (35/35, 100%: FIG. 4). Mean O.D. values to rLinJ16.1750r2 and rK39 were 1.159 and 1.771, respectively.

Figure 5:
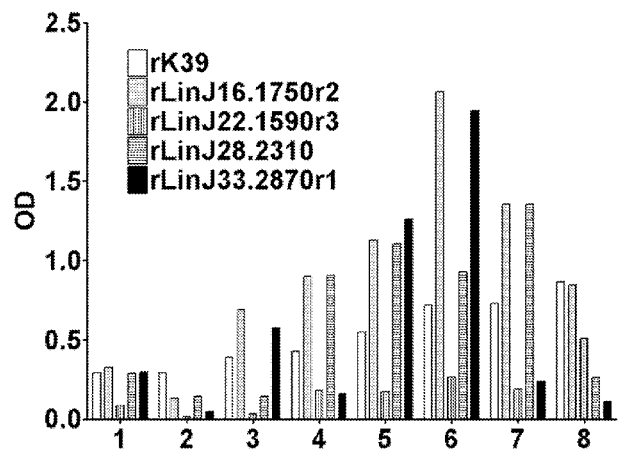
FIG. 5 illustrates exemplary recognition of recombinant proteins by sera from eight visceral leishmaniasis patients, which showed low reactivity to rK39 (OD<1.0, circled in FIG. 4).

Although these 35 sera were 100% positive using rK39, eight sera showed low reactivity to rK39 (OD values were <1.0: FIG. 4). These eight samples were tested for reactivity to rLinJ16.1750r2, rLinJ22.1590r3, rLinJ28.2310 or rLinJ33.2870r1 to examine whether or not those antigens could complement rK39 for more sensitive antibody detection. Five of the eight sera showed better responses to the new antigens than to rK39 (No. 3-7 in FIG. 5). Five patients (No. 3-7) showed better responses to rLinJ22.1590r3, four (No. 4-7) to rLinJ28.2310, and three (No. 3, 5 and 6) to rLinJ33.2870r1. rLinJ22.1590r3 was recognized weakly by all the eight sera compared to rK39.

DNA sequences of 8,191 *L. infantum* genes were obtained from *L. infantum* GeneDB www.genedb.org/genedb/linfantum/index.jsp). Tandem Repeats Finder, a program used to locate and display tandem repeats in DNA sequences, was used for this analysis tandem.bu.edu/trf/trf.html). The program calculates the score according to the nature of the tandem repeat genes such as the period size of the repeat, the number of copies aligned with the consensus pattern and the percent of matches between adjacent copies overall. Thus, an output of a high score in gene analysis means the gene possesses a large tandem repeat sequence and the repeat is highly conserved among the copies. A low score means the opposite; for example, a score of a gene with 3.6 copies of a 36 bp repeat was 111. In this study, the genes were regarded as tandem repeat genes if the scores from the Tandem Repeats Finder analysis were higher than 500, thus excluding genes containing small tandem repeat motifs. Using these screening parameters, the following genes were identified from the *L. infantum* GeneDB. (Table 3)

TABLE III

*L. infantum* TR genes identified by Tandem Repeats Finder

| Gene ID1 | C/I2 | Product | Size (kDa) | PS3 (bp) | CN3 | Score3 | Ref4 |
|---|---|---|---|---|---|---|---|
| LinJ03.0120 | C | hypothetical protein | 237 | 117 | 31.8 | 7033 | 1 |
| LinJ05.0340 | C | viscerotropic leishmaniasis antigen | 95 | 99 | 13.8 | 2545 | 2 |
| LinJ05.0380 | C | microtubule-associated protein | 165 | 114 | 28.5 | 6336 | 1 |
| LinJ09.0950 | C | polyubiquitin | 74 | 228 | 8 | 3621 | |
| LinJ11.0070 | C | hypothetical protein | 147 | 138 | 12.9 | 2435 | |
| LinJ13.0780 | C | hypothetical protein | 107 | 63 | 14.2 | 1637 | |
| LinJ14.0370 | C | hypothetical protein | 302 | 84 | 10.9 | 1475 | |
| LinJ14.1160 | C | kinesin K39 | 242 | 117 | 27.9 | 5237 | 1, 3 |
| LinJ14.1180 | I | kinesin K39 | 278 | 168 | 8.2 | 2671 | |
| LinJ14.1190 | I | kinesin K39 | 95 | 315 | 6.1 | 2828 | 1 |
| LinJ14.1200 | C | kinesin K39 | 79 | 468 | 3.4 | 1971 | 3 |
| LinJ14.1210 | I | kinesin K39 | 337 | 483 | 10.9 | 3676 | |
| LinJ14.1540 | C | hypothetical protein | 112 | 72 | 6.1 | 806 | 1 |
| LinJ15.0490 | I | tb-292 membrane associated | | 105 | 31.6 | 6027 | 1 |
| LinJ15.1570 | I | | 112 | 105 | 29.9 | 5588 | |
| LinJ16.1540 | C | kinesin | 230 | 42 | 138.5 | 10588 | 1 |
| LinJ16.1750 | C | hypothetical protein | 346 | 219 | 8.7 | 3691 | 1 |
| LinJ18.1030 | C | Hypothetical repeat protein | 46 | 21 | 30.4 | 1036 | |
| LinJ19.0940 | C | | 24 | 6 | 95 | 1076 | |
| LinJ19.1560 | I | | 166 | 81 | 21.1 | 3094 | |
| LinJ20.1220 | C | calpain-like cysteine peptidase | 112 | 39 | 11.3 | 826 | |
| LinJ21.2010 | C | hypothetical protein | 306 | 192 | 5.3 | 2003 | |
| LinJ22.0410 | C | hypothetical protein | 130 | 183 | 15.9 | 5779 | |
| LinJ22.0680 | C | hypothetical protein | 45 | 216 | 5.9 | 1240 | 1, 4 |
| LinJ22.1510 | C | hypothetical protein | 179 | 81 | 13.5 | 1984 | |
| LinJ22.1520 | C | | 72 | 39 | 42.9 | 3197 | |
| LinJ22.1550 | C | | 126 | 81 | 10.4 | 1504 | |
| LinJ22.1560 | I | | 172 | 267 | 16.9 | 8614 | |
| LinJ22.1570 | C | | 210 | 81 | 23.5 | 3230 | |
| LinJ22.1580 | C | | 175 | 267 | 17.1 | 8591 | |
| LinJ22.1590 | C | hypothetical protein | 234 | 84 | 29.2 | 3993 | 1 |
| LinJ23.1180 | C | hydrophilic surface protein (HASPB) | 26 | 42 | 11.2 | 832 | 5 |
| LinJ25.1100 | C | hypothetical protein | 91 | 66 | 9.5 | 1142 | |
| LinJ25.1910 | C | hypothetical protein | 91 | 369 | 2 | 1443 | |
| LinJ26.2140 | C | hypothetical protein | 215 | 48 | 63.4 | 5289 | |
| LinJ27.0140 | I | kinetoplast-associated protein-like | 33 | 30 | 19.9 | 1086 | |
| LinJ27.0170 | C | kinetoplast-associated protein-like | 95 | 30 | 62.1 | 3283 | |
| LinJ27.0400 | C | calpain-like cysteine peptidase | 687 | 204 | 43.8 | 17362 | |
| LinJ28.2310 | C | glycoprotein 96-92 | 61 | 315 | 2.2 | 1398 | 1 |
| LinJ28.3170 | C | hypothetical protein | 75 | 60 | 23.4 | 2546 | 1 |
| LinJ29.0110 | C | hypothetical protein | 278 | 24 | 28.6 | 967 | |
| LinJ30.0400 | C | hypothetical protein | 56 | 117 | 7.4 | 1716 | |
| LinJ31.1820 | C | hypothetical protein | 49 | 75 | 4.1 | 581 | |
| LinJ31.1840 | C | hypothetical protein | 52 | 24 | 18.1 | 814 | |
| LinJ31.2660 | C | hypothetical protein | 247 | 456 | 2.2 | 1973 | |
| LinJ31.3360 | C | hypothetical protein | 71 | 30 | 11.1 | 556 | |
| LinJ32.2730 | C | hypothetical protein | 173 | 150 | 10.3 | 2916 | 1 |
| LinJ32.2780 | C | membrane associated protein-like | 132 | 30 | 60.9 | 3125 | 1 |
| LinJ32.3710 | C | hypothetical protein | 292 | 99 | 3.9 | 730 | |

TABLE III-continued

L. infantum TR genes identified by Tandem Repeats Finder

| Gene ID1 | C/I2 | Product | Size (kDa) | PS3 (bp) | CN3 | Score3 | Ref4 |
|---|---|---|---|---|---|---|---|
| LinJ33.2870 | C | hypothetical protein | 413 | 444 | 7 | 6041 | 1 |
| LinJ34.0710 | I | hypothetical protein |  | 336 | 9.5 | 4517 | 1 |
| LinJ34.2140 | C | hypothetical protein | 296 | 249 | 7.4 | 3604 | 1 |
| LinJ34.4250 | C | hypothetical protein | 168 | 168 | 6.1 | 1960 |  |
| LinJ35.0590 | C | proteophosphoglycan ppg4 | 536 | 45 | 246.1 | 10667 | 1 |
| LinJ35.0600 | I | proteophosphoglycan ppg3 |  | 135 | 37.8 | 8773 | 1 |
| LinJ35.0610 | C | proteophosphoglycan ppg4 | 291 | 45 | 183.2 | 13275 |  |
| LinJ35.0620 | I | proteophosphoglycan 5 | 495 | 90 | 152.5 | 15050 |  |
| LinJ35.0630 | I | proteophosphoglycan ppg4 | 281 | 45 | 176.6 | 10813 |  |
| LinJ35.0640 | I | hypothetical protein | 95 | 45 | 58.4 | 4766 |  |
| LinJ35.1530 | C | hypothetical protein | 328 | 141 | 2.4 | 661 |  |
| LinJ35.1620 | I | hypothetical protein |  | 126 | 8.7 | 1855 |  |
| LinJ35.4500 | C | hypothetical protein | 60 | 165 | 4.5 | 1438 |  |
| LinJ36.0320 | C | histidine secretory acid phosphatase | 71 | 72 | 6.5 | 861 |  |
| LinJ36.5810 | C | hypothetical protein | 365 | 276 | 4.3 | 2341 |  |

The following notes correspond to the superscript notes in Table III: (1) ID numbers in GeneDB are temporary and may vary; (2) C or I mean the gene is a complete or incomplete gene, respectively; (3) Data of PS, CN and score in TR analysis are from a program analysis using Tandem Repeats Finder. TR genes are shown in bold letters. Blanks in PS, CN and Score columns represent no repeat found in the genes. PS: period size (bp) of the repeat, CN: number of copies aligned with the consensus pattern; and (4) antigenicity of the protein has been reported in the referenced paper.

Example 12

Analysis of Amino Acid Compositions of Tandem Repeat Proteins

Tandem repeat proteins, which encoded by the tandem repeat genes identified by the bioinformatic analysis, were analyzed their isometric points and amino acid compositions using a software, EditSeq (DNASTAR Inc., Madison, Wis.). Lysine and Arginine were classified as strongly basic amino acids, Aspartic Acid and Glutamic Acid as strongly acidic amino acids, Asparagine, Cysteine, Glutamine, Sering, Threonine and Tyrosine as other polar amino acids, and Alanine, Isoleucine, Leucine, Phenylalanine, Tryptophan and Valine as hydrophobic amino acids. Tandem repeat domains of the tandem repeat proteins were analyzed in a same way. As a control, 108 genes, which were randomly selected from the L. infantum gene database, were also analyzed isometric points and amino acid compositions of their deduced amino acid sequences.

Example 13

Expression of Recombinant Proteins

Sequences encoding whole or partial tandem repeat domains of LinJ20.1220, LinJ25.1100, LinJ32.3710 were amplified by PCR. The amplified PCR products were inserted into multi cloning sites of pET28a and the inserts were confirmed their sequences matching with the ones on database. The vectors with the inserts were transformed into expression host E. coli and the recombinant proteins were purified as 6×His-tagged proteins using Ni-NTA agarose (Qiagen Inc., Valencia, Calif.). The concentrations of these proteins were measured by BCA protein assay (Pierce Biotechnology Inc., Rockford, Ill.).

Example 14

Recognition of Tandem Repeat Proteins by Sera From Leishmaniasis Patients

To evaluate antigenicity of the tandem repeat proteins, ELISA was performed using 200 ng antigen per well in 96-well plates. Sera from visceral Leishmaniasis patients (Sudan), cutaneous leishmaniasis patients (Brazil) and healthy individuals (United States) were used at 1:100 dilutions for the ELISA.

Figure 6:
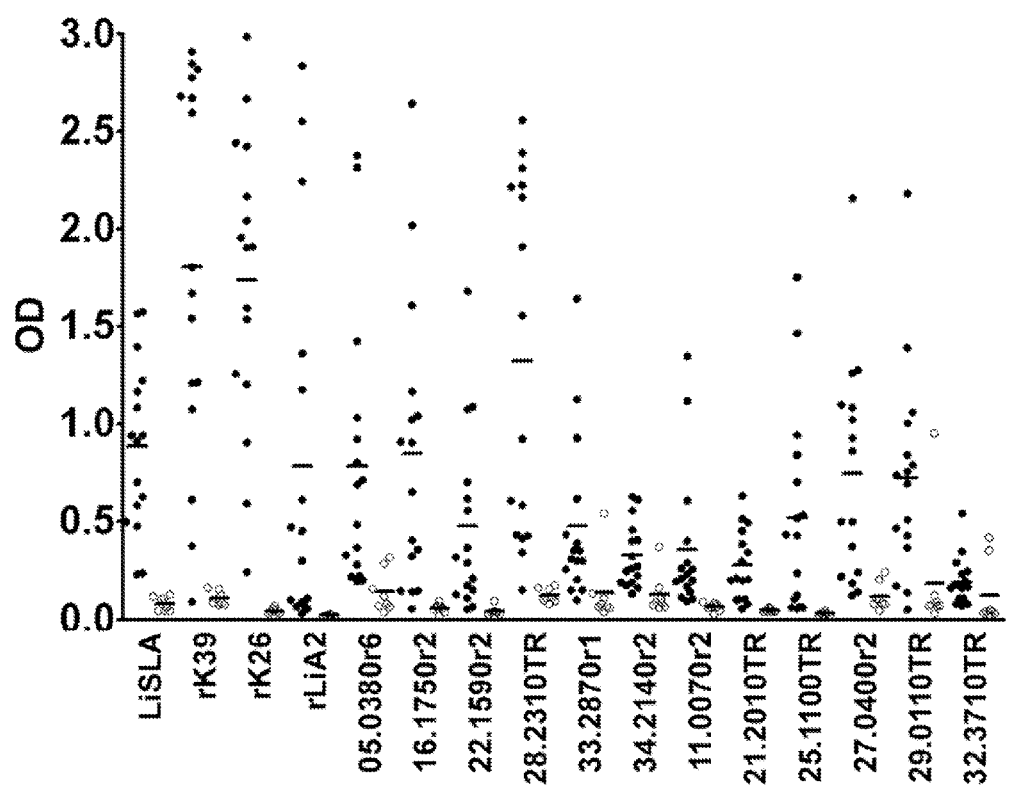
FIG. 6 shows demonstrative antibody responses of visceral leishmaniasis patient sera to tandem repeat proteins. Sera from visceral leishmaniasis patients (closed circles: n=16) and healthy controls (open circles: n=8) were tested for their reactivity to tandem repeat proteins by ELISA and OD values of each individuals are shown. Bars represent means of each group.

The visceral Leishmaniasis patient sera showed significantly stronger reactivity to all the recombinant proteins than sera from non-visceral Leishmaniasis groups, i.e. tuberculosis, malaria and cutaneous leishmaniasis patients or healthy individuals, despite the finding that cutaneous leishmaniasis patients showed antibody responses to LiSLA (FIG. 6). Among the tested proteins, rLinJ16.1750r2 was the best antigen, and was recognized strongly by visceral Leishmaniasis patient sera with a high degree of specificity. Next, rLinJ16.1750r2 was tested with additional Sudanese visceral Leishmaniasis patient sera. Among 35 sera tested, 34 showed antibody responses to rLinJ16.1750r2 (the cutoff value was the mean+3 SD of healthy controls: FIG. 6). The sensitivity using rLinJ16.1750r2 was 97%, comparable to that of rK39 (35/35, 100%: FIG. 6). Mean O.D. values to rLinJ16.1750r2 and rK39 were 1.159 and 1.771, respectively.

Although these 35 sera were 100% positive using rK39, eight sera showed low reactivity to rK39 (OD values were <1.0: FIG. 6). These eight samples were tested for reactivity to rLinJ16.1750r2, rLinJ22.1590r3, rLinJ28.2310 or rLinJ33.2870r1 to examine whether or not those antigens could complement rK39 for more sensitive antibody detection. Five of the eight sera showed better responses to the new antigens than to rK39 (No. 3-7 in FIG. 6). Five patients (No. 3-7) showed better responses to rLinJ22.1590r3, four (No. 4-7) to rLinJ28.2310, and three (No. 3, 5 and 6) to rLinJ33.2870r1. Finally, rLinJ22.1590r3 was recognized weakly by all the eight sera compared to rK39.

Example 15

ELISA Analysis of Tandem Repeat Proteins Identified by Serological Screening and Bioinformatic Analysis Recombinant tandem repeat proteins or L. infantum promastigote soluble lysate antigen (LiSLA) were diluted in ELISA coating buffer, and 96-well plates were coated with rK39 (50 ng), other recombinant proteins (200 ng) or LiSLA (1 μg) followed by blocking with phosphate-buffered saline containing 0.05% Tween-20 and 1% bovine serum albumin. Next, the plates were incubated with patient sera (n=16) as well as healthy controls (n=8) at 1:100 dilution and then with horseradish peroxidase-conjugated anti-human IgG (Rockland Immunochemicals, Inc., Gilbertsville, Pa.). The plates were developed with TMB peroxidase substrate (KPL) and read by a microplate reader at a 450 nm wavelength (570 nm as a reference).

Compared to healthy controls, higher levels of antibody were detected being bound to tandem repeat proteins not only from serological screening but also solely from the bioinformatic analysis in VL patients (Table IV) (FIG. 6). This demonstrates that tandem repeat proteins not only from serological screening but also identified solely by the bioinformatic analysis are antigenic.

TABLE IV

Reactivity of L. infantum Tandem Repeat proteins in ELISA

| Recombinant | PSa (aa) | CNa | Size (kDa) | OD: VL | OD: HC | OD: P value |
|---|---|---|---|---|---|---|
| Identified by serology | | | | | | |
| rLinJ05.0380r6 | 38 | 6 | 28 | 0.786 | 0.142 | ** |
| rLinJ16.1750r2 | 73 | 2 | 18 | 0.847 | 0.058 | *** |
| rLinJ22.1590r3 | 28 | 3 | 12 | 0.474 | 0.042 | *** |
| rLinJ28.2310TR | 105 | 2.2 | 35 | 1.326 | 0.123 | *** |
| rLinJ33.2870r1 | 148 | 1 | 18 | 0.476 | 0.137 | ** |
| rLinJ34.2140r2 | 83 | 2 | 20 | 0.327 | 0.126 | ** |
| Identified solely from bioinformatics | | | | | | |
| rLinJ11.0070r2 | 46 | 2 | 12 | 0.359 | 0.065 | *** |
| rLinJ21.2010TR | 64 | 5.3 | 38 | 0.274 | 0.048 | *** |
| rLinJ25.1100TR | 22 | 9.6 | 27 | 0.520 | 0.032 | *** |
| rLinJ27.0400r2 | 68 | 2 | 18 | 0.748 | 0.117 | *** |
| rLinJ29.0110TR | 8 | 28.8 | 31 | 0.724 | 0.185 | ** |
| rLinJ32.3710TR CRUDE | 33 | 3.8 | 17 | 0.192 | 0.124 | * |
| LiSLA | | | | 0.885 | 0.082 | *** |

Notes:
aPS: length of one copy of the repeat in units of amino acids,
CN: copy number.
bMean OD values of VL patients (VL: n = 16) and healthy controls (HC: n = 8) are shown.
P values are from statistical analyses using Mann-Whitney test.
*P < 0.05,
**P < 0.01.
***P < 0.001.

From the foregoing, it will be appreciated that, although specific embodiments of this invention have been described herein for the purposes of illustration, various modifications may be made without departing from the spirit and scope of the invention. Accordingly, the invention is not limited except by the appended claims.

What is claimed is:

1. A method of screening for antigenic polypeptides for the diagnosis, or treatment of leishmaniasis in a patient, or immunization against leishmaniasis in a patient or screening for *Leishmania* in a blood supply comprising:
   (a) constructing a polynucleotide screening library;
   (b) expressing the expression products of (a);
   (c) screening the expression product of the screening library by
   contacting the expression product with a *Leishmania* specific antibody from a patient or blood supply and detecting an antigenic polypeptide by detecting binding of the expression product and an antibody binding site portion of said *Leishmania* specific antibody; and
   (d) analyzing sequences identified from screening the expression product of the screening library to select genes that are tandem repeat genes and thereby selecting antigenic polypeptides that comprise tandem repeats.

2. The method of claim 1, further comprising the step of excluding polynucleotides having tandem repeat motifs that have a consecutive 8 amino acids or less when analyzing genes identified from the screening library to select genes that are tandem repeat genes.

3. The method of claim 1 wherein the screening library is constructed from *L. Infantum*.

4. A method of screening for antigenic polypeptides for the diagnosis, or treatment of leishmaniasis in a patient, or immunization against leishmaniasis in a patient or screening for *Leishmania* in a blood supply comprising:
   (a) selecting one or more polypeptide sequence or polynucleotide sequence;
   (b) analyzing the selected one or more polypeptide sequence or polynucleotide sequence and selecting sequences that comprise tandem repeats;
   (c) expressing the selected sequences of (b); and
   (d) screening an expression product of (c) by exposing the expression product to a *Leishmania* specific antibody isolated from one or more biological sample obtained from one or more patient infected by *Leishmania* and detecting an antigenic polypeptide by detecting binding of the expression product and an antibody binding site portion of said *Leishmania* specific antibody and thereby selecting antigenic polypeptides.

5. The method of claim 4 wherein the antigenic polypeptides are used for the diagnosis or treatment of, or detection of or immunization against leishmaniasis.

6. The method of claim 1, claim 2, claim 3, claim 4 or claim 5, further comprising the step of screening the selected antigenic polypeptides by comparing the homology of the sequences of the selected antigenic polypeptides to the sequences of polypeptides of organisms that are potentially infected by *Leishmania* and thereby selecting one or more polypeptides that are least homologous to polypeptides of organisms that are potentially infected by *Leishmania*.

7. The method of claim 1, claim 2, claim 3, claim 4 or claim 5, further comprising the step of screening the selected antigenic polypeptides by comparing the homology of the sequences of the selected antigenic polypeptides to the sequences of polypeptides of organisms that potentially infect organisms that are potentially infected by *Leishmania* and thereby selecting one or more polypeptides that are least homologous to polypeptides of organisms that potentially infect organisms that are potentially infected by *Leishmania*.

8. A method of identifying candidate antigenic polypeptides for the diagnosis, or treatment of leishmaniasis in a patient, or immunization against leishmaniasis in a patient or screening for *Leishmania* in a blood supply, comprising:
   (a) expressing, in one or a plurality of host cells, expression products of a polynucleotide expression library which comprises one or a plurality of candidate antigenic polypeptide-encoding polynucleotides at least one of which is capable of expressing a candidate antigenic polypeptide that comprises a tandem repeat, to obtain a host cell population comprising expression products;
   (b) contacting, under conditions and for a time sufficient for specific binding of at least one *Leishmania* specific antibody isolated from a biological sample from a patient or blood supply to at least one expression product, (i) the host cell population comprising expression products of (a) with (ii) said antibody that is obtained from a subject or biological source that has been infected with a *Leishmania* organism, wherein the biological material is selected from blood, serum and urine;

(c) detecting at least one host cell that comprises the at least one expression product to which the at least one anti-Leishmania antibody specifically binds;

(d) isolating from the host cell detected in (c) a polynucleotide that encodes the expression product to which the at least one anti-Leishmania antibody specifically binds to obtain an isolated polynucleotide; and (e) analyzing a nucleotide sequence of the isolated polynucleotide of (d) for presence or absence of a tandem repeat, wherein the presence of a tandem repeat indicates the isolated polynucleotide encodes an antigenic polypeptide, and therefrom identifying the antigenic polypeptide.

9. The method of claim 8 wherein the polynucleotide expression library is constructed from nucleic acid sequences obtained from an organism that is selected from an infectious organism and a non-infectious organism.

10. The method of claim 8 wherein the polynucleotide expression library is constructed from an organism that causes leishmaniasis.

11. The method of claim 10 wherein the organism that causes leishmaniasis is selected from the group consisting of *Leishmania infantum, Leishmania* donovani, *Leishmania major, Leishmania* amazonensis, and a bacterial strain that causes leishmaniasis.

12. The method of claim 8 wherein the polynucleotide expression library is constructed from a pathogenic or non-pathogenic microbial organism that is selected from the group consisting of a bacterium, a virus, a protozoan, a fungus, a yeast, a diplomonadid and a kinetoplastid.

13. A method of identifying a candidate antigenic polypeptide for the diagnosis, or treatment of leishmaniasis in a patient, or immunization against leishmaniasis in a patient or screening for *Leishmania* in a blood supply, comprising:

(a) expressing, in one or a plurality of host cells, expression products of a polynucleotide expression library which comprises one or a plurality of candidate antigenic polypeptide-encoding polynucleotides at least one of which is capable of expressing a candidate antigenic polypeptide that comprises a tandem repeat, to obtain a host cell population comprising expression products;

(b) contacting, under conditions and for a time sufficient for specific binding of at least one *Leishmania* specific antibody isolated from the biological material to at least one expression product, (i) the host cell population comprising expression products of (a) with (ii) said at least one antibody that is obtained from a subject or biological source that has been infected with an infectious organism, wherein the biological material is selected from blood, serum and urine;

(c) detecting at least one host cell that comprises the at least one expression product to which the at least one anti-Leishmania antibody specifically binds;

(d) isolating from the host cell detected in (c) a polynucleotide that encodes the expression product to which the at least one anti-Leishmania antibody specifically binds to obtain an isolated polynucleotide; and (e) analyzing a nucleotide sequence of the isolated polynucleotide of (d) for presence or absence of a tandem repeat, wherein the presence of a tandem repeat indicates the isolated polynucleotide encodes an antigenic polypeptide, and therefrom identifying the antigenic polypeptide.

14. The method of claim 13 wherein the polynucleotide expression library is constructed from nucleic acid sequences obtained from an organism that is selected from an infectious organism and a non-infectious organism.

15. The method of claim 13 wherein the polynucleotide expression library is constructed from an organism that causes leishmaniasis.

16. The method of claim 15 wherein the organism that causes leishmaniasis is selected from the group consisting of *Leishmania infantum, Leishmania* donovani, *Leishmania major, Leishmania* amazonensis, and a bacterial strain that causes leishmaniasis.

17. The method of claim 13 wherein the polynucleotide expression library is constructed from a pathogenic or non-pathogenic microbial organism that is selected from the group consisting of a bacterium, a virus, a protozoan, a fungus, a yeast, a diplomonadid and a kinetoplastid.

* * * * *